(12) United States Patent
Park

(10) Patent No.: US 7,838,826 B1
(45) Date of Patent: Nov. 23, 2010

(54) APPARATUS AND METHOD FOR PARALLEL FLOW ION MOBILITY SPECTROMETRY COMBINED WITH MASS SPECTROMETRY

(75) Inventor: Melvin A. Park, Billerica, MA (US)

(73) Assignee: Bruker Daltonics, Inc., Billerica, MA (US)

( * ) Notice: Subject to any disclaimer, the term of this patent is extended or adjusted under 35 U.S.C. 154(b) by 102 days.

(21) Appl. No.: 12/187,924

(22) Filed: Aug. 7, 2008

(51) Int. Cl.
*H01J 49/06* (2006.01)
*H01J 49/40* (2006.01)

(52) U.S. Cl. .................. 250/288; 250/287; 250/281; 250/182; 250/283; 250/396 R; 250/423 R

(58) Field of Classification Search ............ 250/288, 250/287, 281, 282, 283, 423 R, 396 R
See application file for complete search history.

(56) References Cited

U.S. PATENT DOCUMENTS

| | | | | |
|---|---|---|---|---|
| 6,107,628 | A * | 8/2000 | Smith et al. | 250/292 |
| 6,486,469 | B1 | 11/2002 | Fischer et al. | |
| 7,087,898 | B2 * | 8/2006 | Willoughby et al. | 250/288 |
| 2002/0175278 | A1 * | 11/2002 | Whitehouse | 250/281 |
| 2002/0175279 | A1 | 11/2002 | Hager | |
| 2006/0108520 | A1 * | 5/2006 | Park et al. | 250/287 |

FOREIGN PATENT DOCUMENTS

WO    WO 2004/109741 A2    12/2004

OTHER PUBLICATIONS

Barnett, et al., "Application of ESI-FAIMS-MS to the Analysis of Tryptic Peptides", J Am Soc Mass Spectrom 2002, 13, 1282-1291, Elsevier Science Inc.
Buryakov, et al., "A New Method of Separation of Multi-Atomic Ions by Mobility at Atmospheric Pressure Using a High-Frequency Amplituded-Asymmetric Strong Electric Field", Int'l J of Mass Spectrom and Ion Processes, 128 (1993) 143-148, Elsevier Science Publishers B.V.
Ells, et al., "Detection of Chlorinated and Brominated Byproducts of Drinking Water Disinfection Using Electrospray Ionization—High-Field Asymmetric Waveform Ion Mobility Spectrometry-Mass Spectrometry", Anal. Chem., 1999, vol. 71, No. 20, pp. 4747-4752, American Chemical Society.

(Continued)

*Primary Examiner*—Nikita Wells
(74) *Attorney, Agent, or Firm*—Law Office of Paul E. Kudirka

(57) ABSTRACT

Analyte ions entrained in a carrier gas are analyzed by parallel flow ion mobility spectrometry prior to analysis by a mass analyzer. An extended ion funnel is located in the vacuum system of the mass analyzer and has an ion focusing section and an ion mobility analyzing section. The carrier gas together with entrained ions is introduced into the ion focusing section where the ions are focused to the axis of the funnel by applied RF voltages. In the ion mobility section, the action of an RF quadrupolar field, the movement of the carrier gas and axial DC field, separates the ions on the basis of their mobilities. The mobility separated ions are released into the mass analyzer where the ions may be further separated on the basis of mass.

22 Claims, 13 Drawing Sheets

OTHER PUBLICATIONS

Page, et al., "Variable Low-Mass Filtering Using an Electrodynamic Ion Funnel", J Mass Spectrom 2005, 40 1215-1222, John Wiley & Sons, Ltd.

Gabryelski, et al., "Rapid and Sensitive Differentiation of Anomers, Linkage, and Position Isomers of Disaccharides using high-Field Asymmetric Waveform Ion Mobility Spectrometry (FAIMS)", Am Soc Mass Spectrom 2003, 14, 265-277, Elsevier Science Inc.

Guevremont, et al., "Comparison of Experimental and Calculated Peak Shapes for Three Cylindrical Geometry FAIMS Prototypes of Differing Electrode Diameters", Am Soc Mass Spectrom 2005, 16, 349-362, Elsevier Inc.

Reigner, et al., "Qualitative Evaluation of Field Ion Spectrometry for Chemical Warfare Agent Detection", 45th ASMS Conference on Mass Spectrometry and Allied Topics, Jun. 1-5, 1997, Palm Springs, CA, US.

Shvartsburg, et al., "FAIMS Operation for Realistic Gas Flow Profile and Asymmetric Waveforms Including Electronic Noise and Ripple", Am Soc Mass Spectrom 2005, 16, 1447-1455, Elsevier Inc.

Shvartsburg, et al., "Optimization of the Design and Operation of FAIMS Analyzers", J Am Soc Mass Spectrom 2005, 16, 2-12, Elsevier Inc.

Srebalus, et al., "Gas-Phase Separations of Electrosprayed Peptide Libraries", Anal. Chem. 1999, 71, 3918-3927.

Taraszka, et al., "Mapping the Proteome of Drosophila Melanogaster: Analysi of Embryos and Adult Heads by LC-IMS-MS Methods", J Proteome Research 2005, 4, 1223-1237.

Wong, et al., "Evaluation of Ion Mobility Spectroscopy for Determining Charge-Solvated Versus Salt-Bridge Structures of Protonated Trimers", Am Soc Mass Spectrom 2005, 16, 1009-1019, Elsevier Inc.

Zeleny, John, "The Distribution of Mobilities of Ions in Moist Air", Physical Review, vol. 34, Jul. 15, 1929, pp. 310-334.

Zeleny, John, "On the The Ratio of the Velocities of the Two Ions producted in Gases by Rontgen Radiation; and on some Related Phenomena", philosophical Magazine, No. 46, pp. 120-154.

* cited by examiner

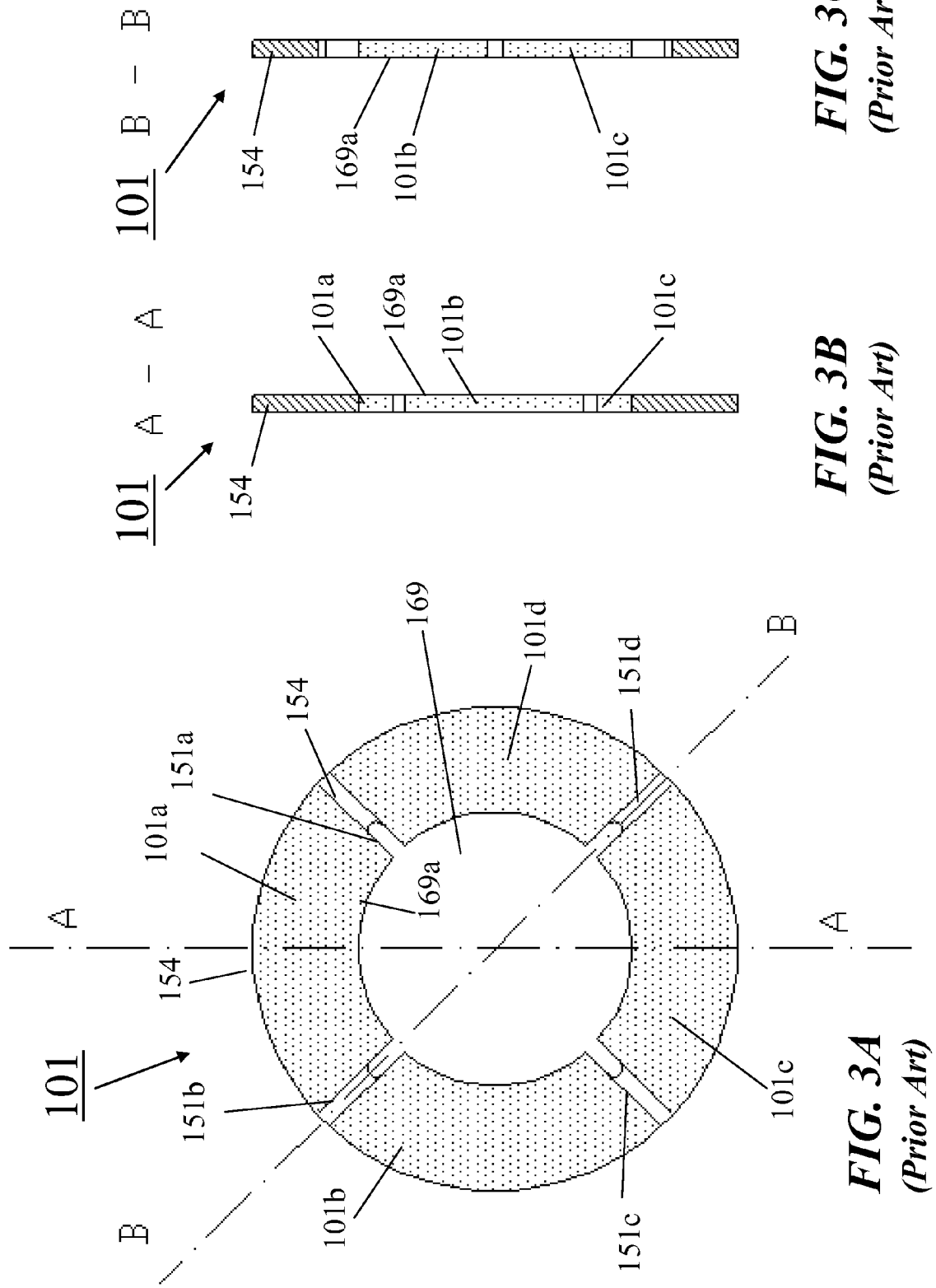

APPARATUS AND METHOD FOR PARALLEL FLOW ION MOBILITY SPECTROMETRY COMBINED WITH MASS SPECTROMETRY

BACKGROUND

The present invention generally relates to an improved method and apparatus for the analysis of gas phase ions by ion mobility spectrometry and by mass spectrometry.

The present invention relates to methods for the analysis of samples by mass spectrometry and by ion mobility. The apparatus and methods for sample handling and analysis described herein are enhancements of the techniques referred to in the literature relating to mass spectrometry and ion mobility spectrometry—important tool in the analysis of a wide range of chemical compounds. Specifically, mass spectrometers can be used to determine the molecular weight of sample compounds. The analysis of samples by mass spectrometry consists of three main steps—formation of gas phase ions from sample material, mass analysis of the ions to separate the ions from one another according to ion mass, and detection of the ions. A variety of means and methods exist in the field of mass spectrometry to perform each of these three functions. The particular combination of the means and methods used in a given mass spectrometer determine the characteristics of that instrument.

To mass analyze ions, for example, one might use magnetic (B) or electrostatic (E) analysis, wherein ions passing through a magnetic or electrostatic field will follow a curved path. In a magnetic field, the curvature of the path will be indicative of the momentum-to-charge ratio of the ion. In an electrostatic field, the curvature of the path will be indicative of the energy-to-charge ratio of the ion. If magnetic and electrostatic analyzers are used consecutively, then both the momentum-to-charge and energy-to-charge ratios of the ions will be known and the mass of the ion will thereby be determined. Other well known mass analyzers are the quadrupole (Q), the ion cyclotron resonance (ICR), the time-of-flight (TOF), and the Paul ion trap analyzers. More recently, linear quadrupole ion traps [J. Schwartz, M. Senko, and J. Syka, *J. Am. Soc. Mass Spectrom.* 13, 659 (2002); J. Hager, *Rapid Commun. Mass Spectrom.* 16, 512 (2002)] have become more wide spread. And a new analyzer, the orbitrap, based on the Kingdon trap [K. Kingdon, *Phys. Rev.* 21, 408 (1923)] was recently described by A. Makarov [Q. Hu et al., *J Mass Spectrom.* 40, 430 (2005)]. The analyzer used in conjunction with the means and method described here may be any of a variety of these.

Before mass analysis can begin, gas phase ions must be formed from a sample material. If the sample material is sufficiently volatile, ions may be formed by electron ionization (EI) or chemical ionization (CI) of the gas phase sample molecules. Alternatively, for solid samples (e.g., semiconductors, or crystallized materials), ions can be formed by desorption and ionization of sample molecules by bombardment with high energy particles. Further, Secondary Ion Mass Spectrometry (SIMS), for example, uses keV ions to desorb and ionize sample material. In the SIMS process a large amount of energy is deposited in the analyte molecules, resulting in the fragmentation of fragile molecules. This fragmentation is undesirable in that information regarding the original composition of the sample (e.g., the molecular weight of sample molecules) will be lost.

For more labile, fragile molecules, other ionization methods now exist. The plasma desorption (PD) technique was introduced by Macfarlane et al. (R. D. Macfarlane, R. P. Skowronski, D. F. Torgerson, *Biochem. Biophys. Res Commoun.* 60 (1974) 616) ("McFarlane"). Macfarlane discovered that the impact of high energy (MeV) ions on a surface, like SIMS would cause desorption and ionization of small analyte molecules. However, unlike SIMS, the PD process also results in the desorption of larger, more labile species (e.g., insulin and other protein molecules).

Additionally, lasers have been used in a similar manner to induce desorption of biological or other labile molecules. See, for example, Cotter et al. (R. B. VanBreeman, M. Snow, R. J. Cotter, *Int. J. Mass Spectrom. Ion Phys.* 49 (1983) 35; Tabet, J. C.; Cotter, R. J., Tabet, J. C., *Anal. Chem.* 56 (1984) 1662; or R. J. Cotter, P. Demirev, I. Lys, J. K. Olthoff, J. K.; Lys, I.: Demirev, P.: Cotter et al., R. J., *Anal. Instrument.* 16 (1987) 93). Cotter modified a CVC 2000 time-of-flight mass spectrometer for infrared laser desorption of non-volatile biomolecules, using a Tachisto (Needham, Mass.) model 215G pulsed carbon dioxide laser. The plasma or laser desorption and ionization of labile molecules relies on the deposition of little or no energy in the analyte molecules of interest.

The use of lasers to desorb and ionize labile molecules intact was enhanced by the introduction of matrix assisted laser desorption ionization (MALDI) (K. Tanaka, H. Waki, Y. Ido, S. Akita, Y. Yoshida, T. Yoshica, *Rapid Commun. Mass Spectrom.* 2 (1988) 151 and M. Karas, F. Hillenkamp, *Anal. Chem.* 60 (1988) 2299). In the MALDI process, an analyte is dissolved in a solid, organic matrix. Laser light of a wavelength that is absorbed by the solid matrix but not by the analyte is used to excite the sample. Thus, the matrix is excited directly by the laser, and the excited matrix sublimes into the gas phase carrying with it the analyte molecules. The analyte molecules are then ionized by proton, electron, or cation transfer from the matrix molecules to the analyte molecules. This process (i.e., MALDI) is typically used in conjunction with time-of-flight mass spectrometry (TOFMS) and can be used to measure the molecular weights of proteins in excess of 100,000 Daltons.

Atmospheric Pressure Ionization (API) includes a number of ion production means and methods. Typically, analyte ions are produced from liquid solution at atmospheric pressure. One of the more widely used methods, known as electrospray ionization (ESI), was first suggested for use with mass spectrometry by Dole et al. (M. Dole, L. L. Mack, R. L. Hines, R. C. Mobley, L. D. Ferguson, M. B. Alice, *J. Chem. Phys.* 49, 2240, 1968). In the electrospray technique, analyte is dissolved in a liquid solution and sprayed from a needle. The spray is induced by the application of a potential difference between the needle and a counter electrode. The spray results in the formation of fine, charged droplets of solution containing analyte molecules. In the gas phase, the solvent evaporates leaving behind charged, gas phase, analyte ions. This method allows for very large ions to be formed. Ions as large as 1 MDa have been detected by ESI in conjunction with mass spectrometry (ESMS).

In addition to ESI, many other ion production methods might be used at atmospheric or elevated pressure. For example, MALDI has recently been adapted by Laiko et al. to work at atmospheric pressure (Victor Laiko and Alma Burlingame, "Atmospheric Pressure Matrix Assisted Laser Desorption", U.S. Pat. No. 5,965,884, and Atmospheric Pressure Matrix Assisted Laser Desorption Ionization, poster #1121, 4$^{th}$ International Symposium on Mass Spectrometry in the Health and Life Sciences, San Francisco, Aug. 25-29, 1998) and by Standing et al. at elevated pressures (Time of Flight Mass Spectrometry of Biomolecules with Orthogonal Injection+Collisional Cooling, poster #1272, 4$^{th}$ International Symposium on Mass Spectrometry in the Health and Life Sciences, San Francisco, Aug. 25-29, 1998; and Orthogonal Injection TOFMS *Anal. Chem.* 71(13), 452A (1999)). The benefit of adapting ion sources in this manner is that the ion optics (i.e., the electrode structure and operation) in the mass analyzer and mass spectral results obtained are largely independent of the ion production method used.

The elevated pressure MALDI source disclosed by Standing differs from what is disclosed by Laiko et al. Specifically, Laiko et al. disclose a source intended to operate at substantially atmospheric pressure. In contrast, the source disclosed by Standing et al. is intended to operate at a pressure of about 70 mtorr.

More recently, Takats et al. [Z. Takats, J. M. Wiseman, B. Gologan, and R. G. Cooks, Science 306, 471 (2004)] introduced yet another atmospheric pressure ionization method known as desorption electrospray ionization (DESI). According to Takats et al., DESI is a method for producing ions from analyte on a surface. Electrosprayed charged droplets and ion of solvent are directed at the surface under study. The impact of the charged droplets on the surface results in the desorption and ionization of the analyte to form gas phase analyte ions.

Analyte ions produced via an API method need to be transported from the ionization region through regions of differing pressures and ultimately to a mass analyzer for subsequent analysis (e.g., via time-of-flight mass spectrometry (TOFMS), Fourier transform mass spectrometry (FTMS), etc.). In some prior art sources, this was accomplished through use of a small orifice between the ionization region and the vacuum region. In other prior art, dielectric capillaries have been used to transmit ions entrained in a carrier gas from a high pressure ion production region into the vacuum chamber of mass spectrometers—see, for example, Fenn et al., U.S. Pat. No. 4,542,293 and Whitehouse et al., U.S. Pat. No. 5,844,237. In U.S. Pat. No. 6,777,672, incorporated herein by reference, Park describes a multiple section capillary for interfacing various ion production means and for transporting ions into the vacuum chamber of a mass spectrometer.

Importantly, ions are carried through the transfer capillary by entrainment in gas which is pumped from the ion production region, through the capillary, into the first vacuum region of the mass spectrometer. Typically, the gas pressure at the capillary inlet is about one atmosphere whereas the pressure at the capillary outlet, into the first pumping region, is between one and three millibar. Under these conditions, the velocity of the gas in the capillary is about 100 m/s. It is the "force" associated with this high velocity gas that is able to drive the ions away from the electrically attractive potential at the capillary entrance and towards the electrically repulsive potential at the capillary exit.

FIG. 1 depicts a prior art capillary 7 as incorporated in a prior art ion source. Capillary 7 extends from ion production region 40, into first vacuum region 35 of an ion source. O-ring 31 forms a seal between capillary 7 and the wall of vacuum region 35. Entrance end 26 of capillary 7 is substantially covered by apertured endcap electrode 33. Endcap 33 is composed of a chemically resistant, electrically conducting material such as stainless steel. When producing positive analyte ions, endcap 33 may be held at a potential of −4 kV and capillary entrance 26 may be held at a potential of −4.5 kV. Solution containing analyte is nebulized via sprayer 36. Sprayer 36 is held at near ground potential. As a result of the potential difference between sprayer 36 and endcap 33, the droplets formed via sprayer 36 are positively charged. Drying gas 27 is introduced into region 40 via the aperture in endcap 33. Solvent in the droplets formed via sprayer 36 evaporates into drying gas 27. Drying gas 27 may be heated to accelerate solvent evaporation. The complete, or near complete, evaporation of solvent from the analyte droplets results in gas phase analyte ions. The analyte ions are attracted by the electric field and by gas flow into entrance end 26 of capillary 7. Solvent is substantially removed from the flow of ions into entrance end 26 by the flow of drying gas 27 counter to the flow of the ions.

Once through capillary 7, the analyte ions are guided by a combination of gas flows and electric fields through differential pumping regions 65 and 67 to the outlet 69 of the ion source. On exiting the source through outlet 69, the ions either directly or indirectly enter the mass analyzer (not shown). In the mass analyzer the ions are mass analyzed and detected so as to yield a mass spectrum. Any known mass analyzer or combination of mass analyzers including time-of-flight, quadrupole, Paul trap, linear ion trap, orbitrap, electric or magnetic sector, or ion cyclotron resonance analyzers might be used.

One type of ion guide used in ion sources is the so called "ion funnel". An ion funnel is disclosed by Smith et al. in U.S. Pat. No. 6,107,628, entitled "Method and Apparatus for Directing Ions and Other Charged Particles Generated at Near Atmospheric Pressures into a Region Under Vacuum". One embodiment, illustrated in FIG. 2, consists of a plurality of elements, or rings 13, each element having an aperture, defined by the ring inner surface 20. At some location in the series of elements, each adjacent aperture has a smaller diameter than the previous aperture, the aggregate of the apertures thus forming a "funnel" shape, otherwise known as an ion funnel. The ion funnel thus has an entry, corresponding with the largest aperture 21, and an exit, corresponding with the smallest aperture 22. According to Smith et al., the rings 13 containing apertures 20 may be formed of any sufficiently conducting material. Preferably, the apertures are formed as a series of conducting rings, each ring having an aperture smaller than the aperture of the previous ring. Further, an RF voltage is applied to each of the successive elements so that the RF voltages of each successive element are 180 degrees out of phase with the adjacent element(s), although other relationships for the applied RF field would likely be appropriate. Under this embodiment, a DC electrical field is created using a power supply and a resistor chain to supply the desired and sufficient voltage to each element to create the desired net motion of ions through the funnel.

In co-pending application Ser. No. 11/219,639, incorporated herein by reference, the present inventor discloses a quadrupolar ion funnel having segmented electrodes. As detailed in the co-pending application by the present inventor, ring shaped electrodes are segmented into arcs as depicted in FIGS. 3A-C. According to the co-pending application, " . . . FIG. 3B shows a cross-sectional view formed at line A-A in FIG. 3A. FIG. 3C shows a cross-sectional view formed at line B-B in FIG. 3A. In the preferred embodiment, segmented electrode 101 includes ring-shaped electrically insulating support 154 having aperture 169 through which ions may pass. Four separate electrically conducting elements 101a-101d are formed on support 154 by, for example, bonding metal foils to support 154. Importantly, elements 101a-101d cover the inner rim 169a of aperture 169 as well as the front and back surfaces of support 154 such that ions passing through aperture 169, will in no event encounter an electrically insulating surface. Notice also slots 151a-151d formed in support 154 between elements 101a-101d. Slots 151a-151d serve not only to separate elements 101a-101d but also removes insulating material of support 154 from the vicinity of ions passing through aperture 169. The diameter of aperture 169, the thickness of segmented electrode 101, and the width and depth of slots 151a-151d may all be varied for optimal performance. However, in this example, the diameter of aperture 169 is 26 mm, the thickness of electrode 101 is 1.6 mm, and the width and depth of slots 151 are 1.6 mm and 3.8 mm, respectively.

Ion mobility spectrometry (IMS) is a method whereby the "mobility" of analyte ions through a gas is measured under the influence of a static electric field. IMS is described in detail in the literature [see, for example, G. Eiceman and Z. Karpas, Ion Mobility Spectrometry (CRC. Boca Raton, Fla. 1994); and Plasma Chromatography, edited by T. W. Carr (Plenum, New York, 1984)]. At low electric field strengths— e.g. a few kilovolts per cm—the speed of analyte ions through a gas is measured. To start the measurement, ions are pulsed into the entrance of the mobility analyzer. In the mobility analyzer, a uniform electric field accelerates the ions towards the end of the analyzer. Collisions with gas in the analyzer tend to dampen the ion motion. The action of the electric field and collision of ions with the gas thus results in an average ion speed through the gas. At the far end of the analyzer, the ions strike a detector and are detected. By measuring the time between the introduction of ions into the analyzer and the detection of the ions, the speed of the ions, and therefore their mobility can be determined.

At low field strengths, the mobility of an ion is a constant relating the speed of the ion to the strength of the electric field. However, at high electric field strengths, the mobility of the ions varies with electric field strength. This gives rise to field asymmetric ion mobility spectrometry (FAIMS)—an extension of IMS which takes advantage of the change in ion mobility at high field strengths. FAIMS is described in detail in the literature [I. Buryakov, E. Krylov, E. Nazarov, and U. Rasulev, Int. J. Mass Spectrom. Ion Phys. 128. 143 (1993); D. Riegner, C. Harden, B. Carnahan, and S. Day, Proceedings of the 45th ASMS Conference on Mass Spectrometry and Allied Topics, Palm Springs, Calif., Jun. 1-4, 1997, p. 473; B. Carnahan, S. Day, V. Kouznetsov, M. Matyjaszczyk, and A. Tarassov, Proceedings of the 41st ISA Analysis Division Symposium, Framingham, Mass., Apr. 21-24, 1996, p. 85; and B. Carnahan and A. Tarassov, U.S. Pat. No. 5,420,424].

In recent years, IMS and FAIMS spectrometers have been combined with mass spectrometry. In U.S. Pat. No. 5,905,258 Clemmer and Reilly combine IMS with a time of flight mass spectrometer (TOFMS). This provides for a first analysis of the ions by IMS followed by a second analysis via TOFMS. Ultimately, this yields a two dimensional plot containing both the mobility and mass of the ions under investigation. The advantages of this type of combined analyzer over a mass spectrometer alone are described in detail in the literature [C. S. Srebalus et al., *Anal. Chem.* 71(18), 3918 (1999); J. A. Taraszka et al., *J. Proteom. Res.* 4, 1223 (2005); R. L. Wong, E. R. Williams, A. E. Counterman, and D. Clemmer, *J. Am. Soc. Mass Spectrom.* 16, 1009 (2005)] and include the separation of chemical background from analyte species for an improved signal-to-noise ratio (S/N), and the separation of ions based on compound class or charge state for easier mass spectral interpretation.

Similarly, in U.S. Pat. No. 6,504,149, for example, Guevremont et al. combine a FAIMS device with a mass spectrometer. As detailed in the literature, a combined FAIMS mass spectrometer has similar advantages as an IMS mass spectrometer [A. Shvartsburg, K. Tang, R. Smith, *J. Am. Soc. Mass Spectrom.* 16, 2 (2005); D. A. Barnett, B. Ells, R. Guevremont, and R. W. Purves, *J. Am. Soc. Mass Spectrom.* 13, 1282 (2002)]. For example, a combined FAIMS mass spectrometer has an improved signal-to-noise ratio over a mass spectrometer alone because the FAIMS device can filter away the chemical background.

Several other methods of IMS separation have been demonstrated in the prior art. For example, J. Zeleny described a parallel flow ion mobility analyzer in "J. Zeleny, *Philos. Mag.* 46, 120(1898)." In Zeleny's instrument, a voltage V is applied between two parallel grids separated by a distance h. Gas and ions flow through the grids parallel to the electric field. The electric field retards the motion of the ions such that the average velocity of ions between the grids is v=EK−u, where E is the electric field strength, K is the ion mobility and u is the air flow velocity. The mobility of the ions can be calculated as K=h/Et+u/E.

In U.S. Pat. No. 5,847,386, incorporated herein by reference, Thompson and Jolliffe suggest an ion mobility method wherein "ions are admitted into an RF multipole with an axial field, in the presence of cooling gas or drift gas, the ion velocity will reach a constant value which is proportional to the axial field. Ions of different size will drift at different velocities dependant on their shape, mass and charge, and be separated in time when they reach the exit of the device. If the exit gate . . . is opened at an appropriate time, only ions of a certain type will be admitted in the following analyzing device or other detector such as a mass spectrometer. This mobility separation may be applied to assist in the analysis of a mixture of ions . . . ."

More recently Page et al. [J. S. Page et al., *J. Mass Spectrom.* 40, 1215 (2005)] and Laboda et al. [U.S. Pat. No. 6,630,662 incorporated herein by reference] employed the parallel flow analyzer method of Zeleny in combination with RF ion optical devices. However, the method of Page et al. results in a non-uniform gas flow—i.e. the flow direction and speed is dependent on both the axial and radial position within the device. Also the DC axial electric field is non-uniform and includes radial components. Furthermore, the RF confining field generated in the Page device includes an axial component. This tends to interfere with the mobility separation and introduces a mass effect to the separation. That is, the RF field has a greater effect on ions of a given mass range and a lesser effect on ions of another. Finally, in the method of Page et al. ions of a selected mobility cannot actually be isolated from ions of greater and lesser mobility. Rather, ions of high mobility are eliminated from a stream of ions having both high and low mobility. Similarly, Laboda does not teach a means and method whereby ions from a continuous ion source can be effectively introduced into an RF device for mobility analysis, how to generate a highly uniform gas flow or axial DC field, that an axial component of the RF field in the mobility analysis region should be avoided or how to eliminate this component of the field.

These shortcomings in prior art devices limit their mobility resolution, the sensitivity of the instruments employing them—i.e. many ions of interest are lost due to poor efficiency in the mobility device—and the accuracy of the mobility determinations. It is, in part, the purpose of the present invention to overcome these prior art limitations.

SUMMARY

It is therefore one purpose of the present invention to provide a means and method for a tandem ion mobility/mass spectrometer (IMS/MS) instrument wherein the IMS device is integrated into the instrument such that the mobility resolution, transmission efficiency, and accuracy of ion mobility determination is improved over prior art parallel flow mobility analyzers as used in conjunction with mass spectrometers.

In a preferred embodiment, the invention consists of an instrument including an extended RF ion funnel having an entrance end and an exit end. The instrument includes a vacuum system having two or more pumping regions. The pumping region occupied by the extended RF ion funnel is maintained at a pressure amenable to ion mobility separations. Ions produced in an ion production region pass into the entrance end of the extended ion funnel, are focused and analyzed in the extended funnel, and pass out of the exit end of the funnel into a downstream pumping region. The extended funnel is composed of quadrupolar segmented ring electrodes having inner diameters according to position within the device such that the entrance end of the extended funnel has a large diameter in order to capture ions and the exit end of the funnel has a small diameter so as to avoid transmitting gas to downstream pumping regions. The extended funnel is constructed so as to have an ion focusing section near the entrance end and a mobility analyzing section near the exit end. Using the quadrupolar ring electrodes a dipolar focusing RF field is generated in the ion focusing section and a quadrupolar RF containment field is generated in the mobility analyzing section with a simple smooth transition between them. In the ion focusing section, a gap between adjacent ring electrodes is left open so as to allow gas to flow between the electrodes, however, in the analyzing section, the gap between electrodes is smaller and is filled with a dielectric or electrically resistive gasket so that gas flows from the higher pressure entrance end to towards the lower pressure exit end. Because the ring electrodes are substantially cylindrically symmetric, the gas flow profile is also cylindrically symmetric about the axis of the device. A laminar gas flow in the analyzer region tends to push entrained ions towards the exit end. A highly uniform axial DC electric field of predetermined strength is established within the analyzing section via the ring electrodes. The axial DC field blocks the passage of ions out of the analyzing section. A packet of ions is generated via the ion production means and allowed to enter the extended funnel. The entrance to the extended funnel is then blocked such that additional ions may not enter. The ion packet becomes trapped in the analyzer section of the device via the action of the gas flow pushing the ions towards the exit end, the action of the axial DC field pushing the ions towards the entrance end, the RF field confining the ions radially. Over a predetermined period of time, the strength of the axial DC field is gradually decreased so that ions of successively higher mobilities are pushed out the exit end of the analyzer section. Ions thereby being separated based on their mobilities pass into downstream pumping regions and eventually to a mass analyzer wherein the ions can be mass analyzed and detected.

The parallel flow ion mobility analyzer according to the present invention may be used in conjunction with any known ion production method including laser desorption (LD), matrix assisted laser desorption ionization (MALDI), electrospray ionization (ESI), chemical ionization (CI), photoionization (PI), or any other known method of producing ions. When used in conjunction with a pulsed ionization source ions may be introduced directly into the extended funnel. However, when using a continuous ionization source such as ESI, the ion beam must be gated. In the preferred embodiment, ions from an ESI source are entrained in a gas stream and introduced into the extended funnel pumping region in a direction orthogonal to the axis of the funnel. Ions are deflected out of the gas stream and into the funnel via a potential applied to a deflection plate. A packet of ions from the ion beam from the ESI source is gated into the funnel by pulsing the potential on the deflection plate. An additional benefit of passing the gas stream orthogonally past the entrance of the extended funnel is that the directional motion of the introduced gas has substantially no effect on the flow of gas in the mobility analyzer section.

In alternate embodiments, a second packet of ions is accumulated in the ion focusing section of the extended funnel at the same time as a first packet of ions is analyzed in the analyzer section of the funnel. Once the first packet of ions has been analyzed and ejected from the analyzer section, the second packet is transferred from the focusing section into the analyzer section. A third packet of ions is then accumulated in the funnel section while the second packet is being mobility analyzed, and so forth. This method of accumulating and analyzing ions has the effect of improving the duty cycle of the instrument. Ions generated by the ESI source during the mobility analysis step are not discarded, but rather are accumulated, thus increasing the efficiency with which ions are used.

In a further alternate embodiment, the mobility analyzer section is further divided into a trapping region and an analysis region. Ions encounter the trapping region first and the analysis region second. In the trapping region, the strength of the axial DC electric field varies as a function of position along the axis of the device with the lowest field strength being near the entrance of the trapping region and the highest field strength being at the end of the trapping region and throughout the analysis region. Ions are initially trapped in the trapping region. The position at which any given ion is trapped is a function of the ion's mobility such that the highest mobility ions are trapped nearest the entrance to the trapping region and the lowest mobility ions are trapped nearest the analysis region. This has the effect of decreasing the charge density of the trapped ions because the ions are trapped in a line rather than a point. This also has the effect, during the mobility analysis, of placing the ions that are next to be ejected from the analyzer nearest the exit of the device. The axial DC electric field strength in the analysis region is substantially uniform and constant. This has the effect of improving the mobility resolution of the device.

In yet further alternate embodiments, a variable opening at the exit end of the extended funnel allows the flow velocity of gas through the analysis section to be varied. The gas flow velocity is important in defining the lowest mobility ion which can be analyzed while staying within the low field limit. When the axial DC electric field strength is within the low field limit, the speed of an ion is proportional to the electric field strength. When an ion is trapped in the mobility analyzer section of the present invention, the effective speed of the ion relative to the gas is the speed of the gas relative to the electrodes. The lowest mobility ions that can be analyzed while staying within the low field limit are therefore those ions which have the velocity of the gas when the low field limit DC is applied.

Increasing the gas flow velocity may also be beneficial in some cases. In some cases two types of ions may have nearly the same mobility within the low field limit, however, at higher field strengths, the mobility of the ions will vary as a function of the field strength. At high field strengths, the mobilities of the two types of ions may differ from one another such that the two species can be resolved. Analyzing the ions at field strengths above the low field limit may thus resolve otherwise inseparable species. The ability to change the gas velocity is thus important to defining the low mobility limit and may be beneficial in working above the low field limit.

Finally, it should be recognized that the parallel flow analyzer of the present invention may be used as a stand alone analyzer—i.e. without a following mass analyzer—or in combination with any other gas phase ion analyzer including any known type of ion mobility analyzer. As a stand alone analyzer, the parallel flow analyzer of the present invention is followed simply by an ion detector. In combination with other analyzers, other devices may be placed between the parallel flow analyzer of the present invention and the following analyzers. Such devices may include, for example, a collision cell, beam focusing elements, beam steerers, RF and/or DC ion optical elements, etc.

BRIEF DESCRIPTION OF THE DRAWINGS

A further understanding of the present invention can be obtained by reference to a preferred embodiment set forth in the illustrations of the accompanying drawings. Although the illustrated embodiment is merely exemplary of systems for carrying out the present invention, both the organization and method of operation of the invention, in general, together with further objectives and advantages thereof, may be more easily understood by reference to the drawings and the following description. The drawings are not intended to limit the scope of this invention, which is set forth with particularity in the claims as appended or as subsequently amended, but merely to clarify and exemplify the invention.

For a more complete understanding of the present invention, reference is now made to the following drawings in which:

FIG. 3A depicts a prior art "segmented" electrode ring includes four electrically conducting segments;

FIG. 3B is a cross-sectional view of the segmented electrode of FIG. 3A formed at line A-A;

FIG. 3C is a cross-sectional view of the segmented electrode of FIG. 3A formed at line B-B;

DETAILED DESCRIPTION

While the invention has been shown and described with reference to a number of embodiments thereof, it will be recognized by those skilled in the art that various changes in form and detail may be made herein without departing from the spirit and scope of the invention as defined by the appended claims.

As required, a detailed illustrative embodiment of the present invention is disclosed herein. However, techniques, systems and operating structures in accordance with the present invention may be embodied in a wide variety of sizes, shapes, forms and modes, some of which may be quite different from those in the disclosed embodiment. Consequently, the specific structural and functional details disclosed herein are merely representative, yet in that regard, they are deemed to afford the best embodiment for purposes of disclosure and to provide a basis for the claims herein which define the scope of the present invention.

The following presents a detailed description of a preferred embodiment of the present invention, as well as some alternate embodiments of the invention. As discussed above, the present invention relates generally to the mass spectroscopic analysis of chemical samples and more particularly to mass spectrometry. Specifically, a means and method is described for the tandem IMS/MS analysis of a sample. Reference is herein made to the figures, wherein the numerals representing particular parts are consistently used throughout the figures and accompanying discussion.

Figure 4A:
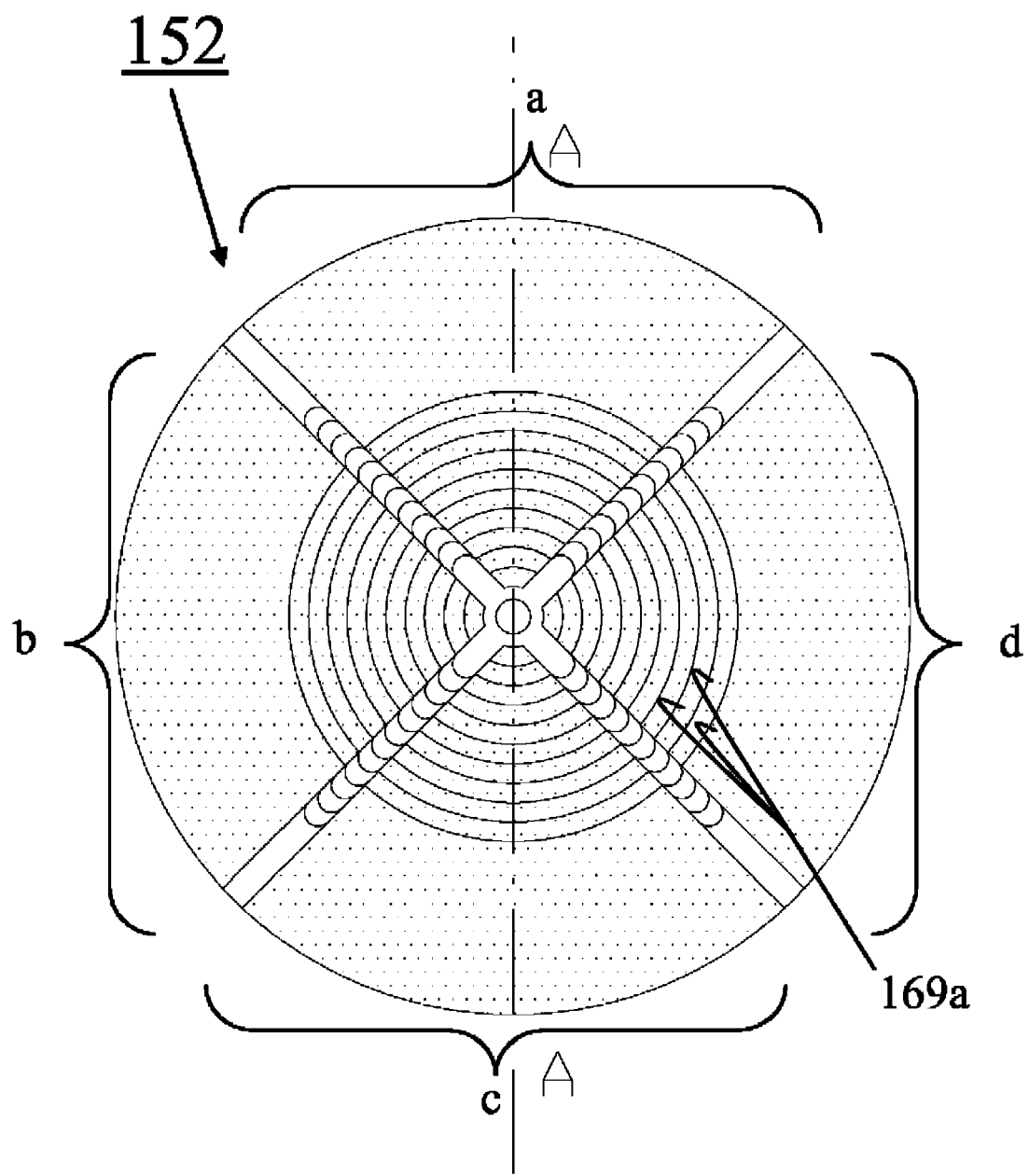
FIG. 4A depicts an end view of a "segmented" funnel according to the present invention constructed from segmented electrodes of the type shown in FIG. 3A.
Figure 4B:
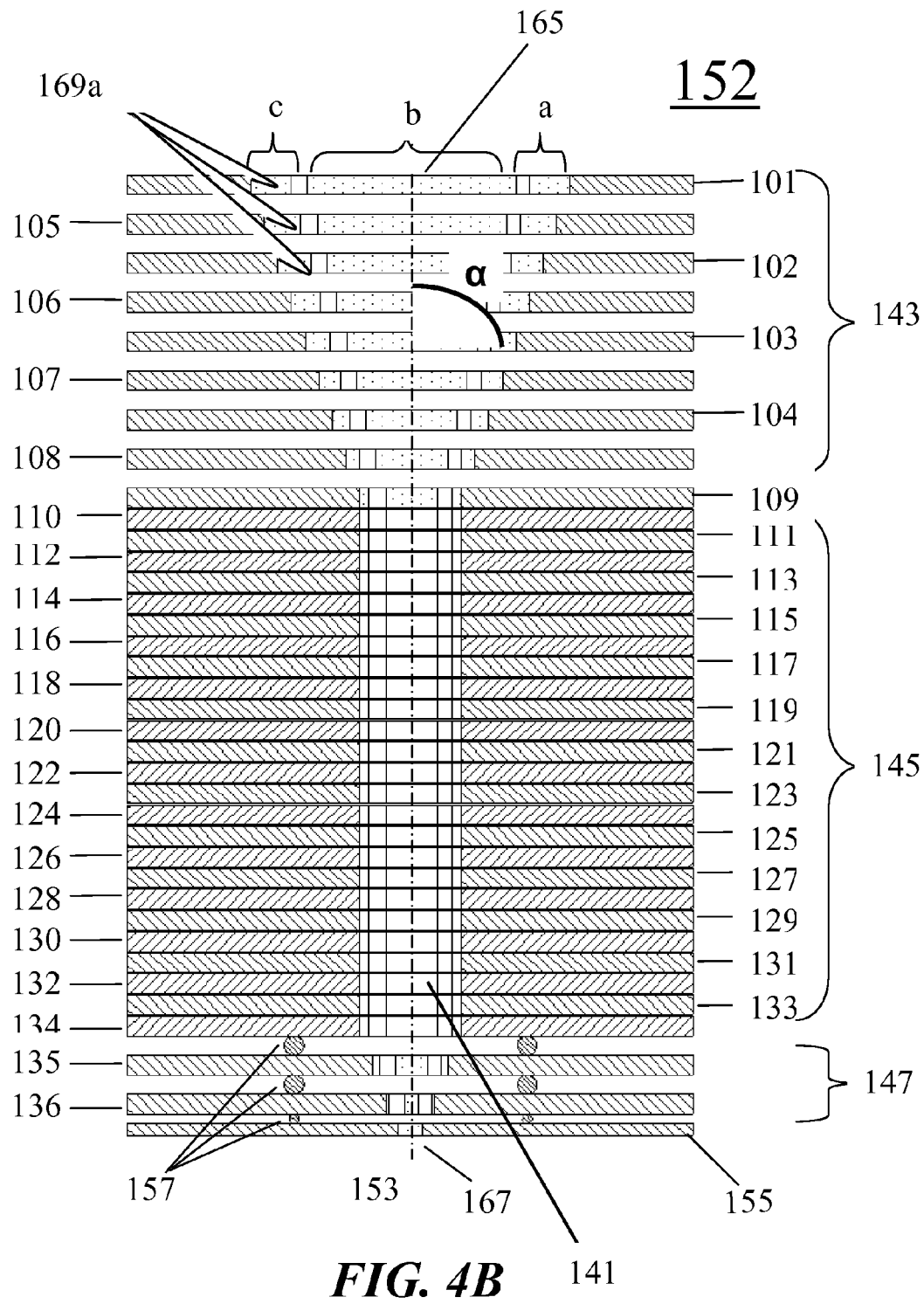
FIG. 4B is a cross-sectional view of the segmented funnel of FIG. 3A formed at line A-A.

Referring to FIGS. 4A and 4B, shown are depictions of the preferred embodiment of the present invention. As shown, extended ion funnel 152 is comprised of a multitude of segmented electrodes 101-136 as described with respect to FIGS. 3A-3C above and in co-pending application Ser. No. 11/219,639. Segmented electrodes 101-136 are assembled about common axis 153. An end view of the set of segmented electrodes 101-136 and exit electrode 155 assembled into extended ion funnel 152 is shown in FIG. 4A. FIG. 4B shows a cross-sectional view formed at line A-A in FIG. 4A. Extended ion guide 152 can be treated as three sections—an entrance focusing section 143, a mobility analysis section 145, and an exit focusing section 147. In focusing regions 143 and 147 of the preferred embodiment, the distances between adjacent electrodes 101-109 and 134-136 is approximately equal to the thickness of the electrodes—in this case 1.6 mm. The diameter of the apertures in electrodes 101-109 and 134-135 is a function of the position of the electrode in ion funnel assembly 152. For example, as depicted in FIG. 4B, the segmented electrode having the largest aperture (in this example segmented electrode 101) is at entrance end 165 of ion funnel 152 and the segmented electrode having the smallest aperture (in this embodiment, segmented electrode 136) is at the exit end 167 of ion funnel 152. The aperture diameter in the preferred embodiment is a linear function of the segmented electrode's position in focusing sections 143 and 147. However, in alternate embodiments this function may be non-linear. Further, in the preferred embodiment, the angle α formed between common axis 153 and the inner boundary (i.e., formed by the inner rims 169a of the segmented electrodes 101-109) of ion funnel 152 is approximately 19°. However, alternatively, any angle between 0° and 90° may be used.

In analysis section 145 of ion funnel 152, the segmented electrodes 109-134 all have the same inner diameter—in this case 8 mm. In analysis section 145 the spacing between adjacent electrodes 109-134 is about 0.1 mm. The space between adjacent electrodes 109-134 is filled with dielectric or electrically resistive gaskets (not shown) composed of, for example, Teflon or polyimide sheet. In alternate embodiments, the segmented electrode inner diameter, the thickness of the segmented electrodes, and the spacing between the electrodes may vary widely, however, the thickness of the segmented electrodes should be much smaller than its inner diameter and the spacing between the electrodes should be smaller than the thickness of the segmented electrodes. As discussed below the thickness of electrodes 109-134 should be much smaller than their inner diameter so that the axial DC field will be homogeneous near the axis. As further discussed below, the spacing between electrodes 109-134 should be smaller than the thickness of the electrodes so as to maintain a uniform RF field.

Gaskets or o-rings 157 between electrodes 134-136 and 155 together with the gaskets between electrodes 109-134 form a substantially air tight seal between electrodes 109-136 and 155. The apertures in electrodes 109-136 and 155 thus form gas tight channel 141 through which gas may flow. When operated according to the preferred method, gas enters channel 141 via the aperture in electrodes 109. The gas forms a laminar stream that flows uniformly through the apertures in electrodes 109-134. The gas flow is then constricted through the apertures in electrodes 135 and 136 and then flows out of extended funnel 152 through the aperture in electrode 155. Notice, as depicted in FIGS. 3 and 4A, that the apertures in electrodes 109-136 and 155 are substantially cylindrically symmetric. This is essential for maintaining a cylindrically symmetric flow profile. In operation, a symmetric laminar flow of gas means that all ions of a given type at a given position along axis 153 will experience a given force due to the gas flow substantially independent of their lateral position with respect to axis 153.

Notice that in section 143 gas may flow freely in the space between adjacent electrodes 101-109. During operation according to the preferred method, gas flow through the space between adjacent electrodes 101-109 assists in the separation of gas—which is pumped away—from ions—which are retained in and transmitted through funnel 152.

Figure 5:
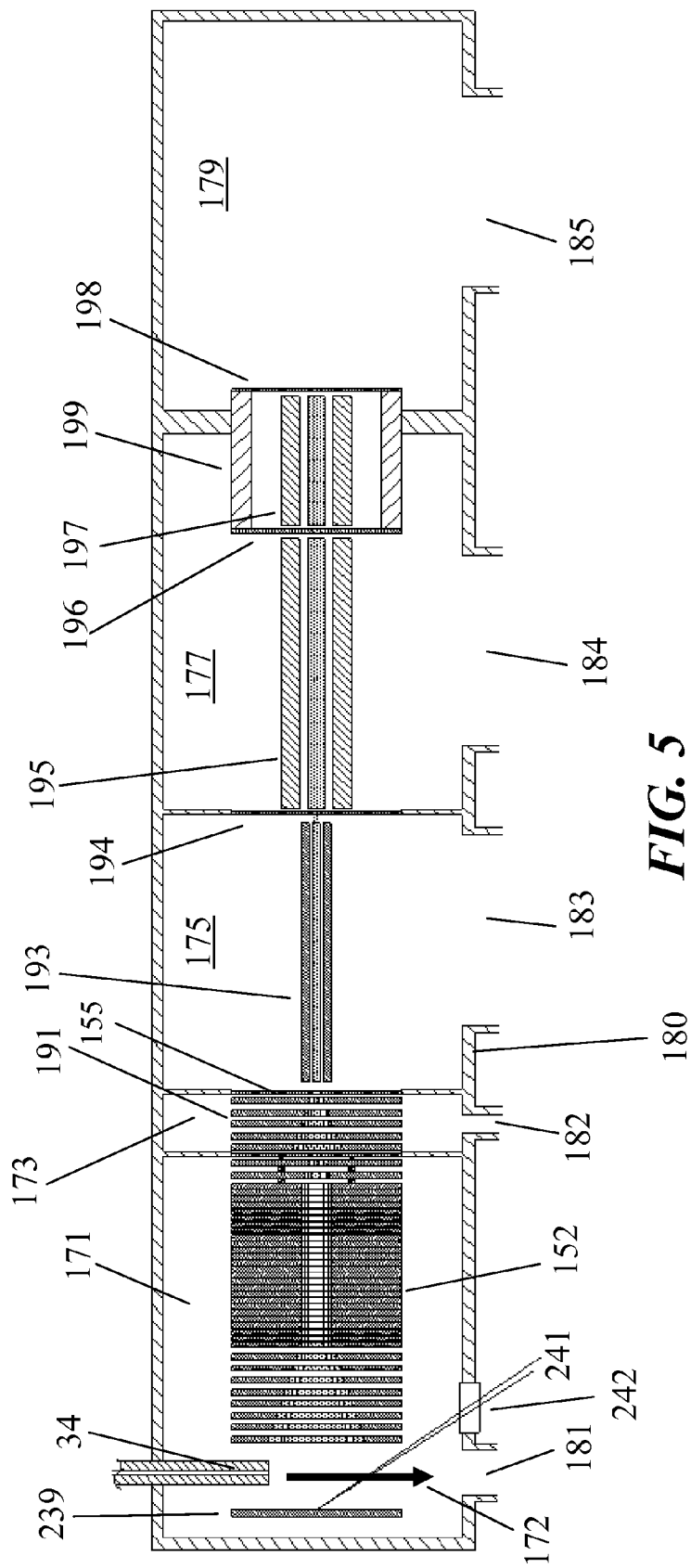
FIG. 5 depicts extended ion funnel assembly 152 incorporated in the vacuum system of a mass spectrometer.

The invention has applicability in a variety of ways in a mass spectrometer system. FIG. 5 depicts extended ion funnel assembly 152 incorporated in the vacuum system of a mass spectrometer. The vacuum system of the mass spectrometer shown consists of housing 180 including five chambers 171, 173, 175, 177 and 179. Although gas pressures in the chambers may vary widely, examples of gas pressures in a system such as this are ~2 mbar in chamber 171, 0.2 mbar in chamber 173, ~$5\times10^{-3}$ mbar in chamber 175, ~$5\times10^{-5}$ mbar in chamber 177, and ~$5\times10^{-7}$ in chamber 179. The operating pressure of an extended ion funnel may be any pressure from $10^{-6}$ mbar up to near atmospheric pressure. However, the pressure in the funnel during a mobility analysis must be sufficient for the mobility analysis—i.e. greater than about 0.01 mbar. To achieve and maintain the desired pressure levels in these chambers, each of chambers 171, 173, 175, 177, and 179 include pumping ports 181, 182, 183, 184, and 185, respectively, through which gas may be pumped away. When incorporated in vacuum housing 180, lens element 155 (FIG. 4B) acts as a pumping restriction between first chamber 171 and second chamber 173.

Figure 1:
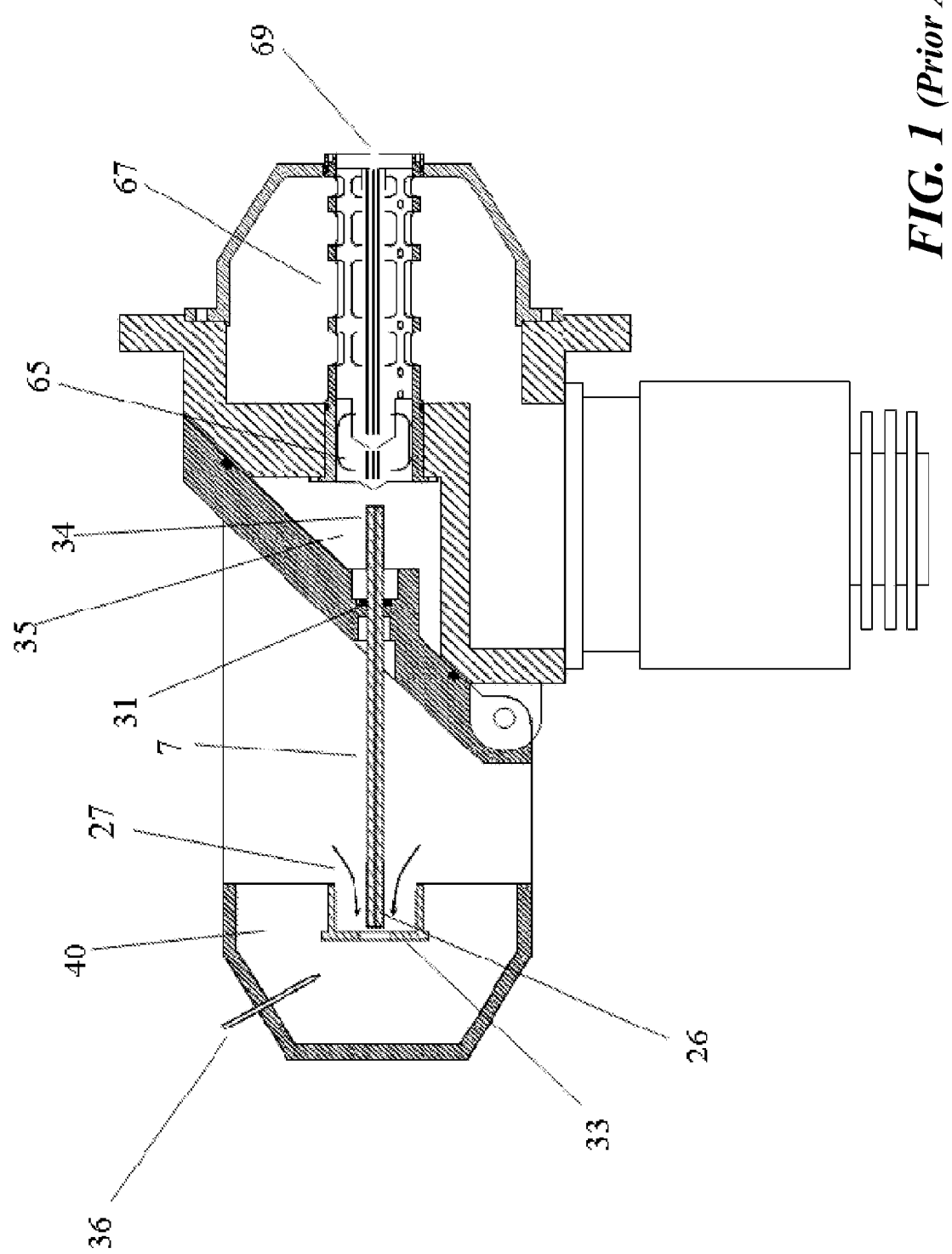
FIG. 1 is a depiction of a prior art API ion source including an ion transfer capillary.
Figure 2:
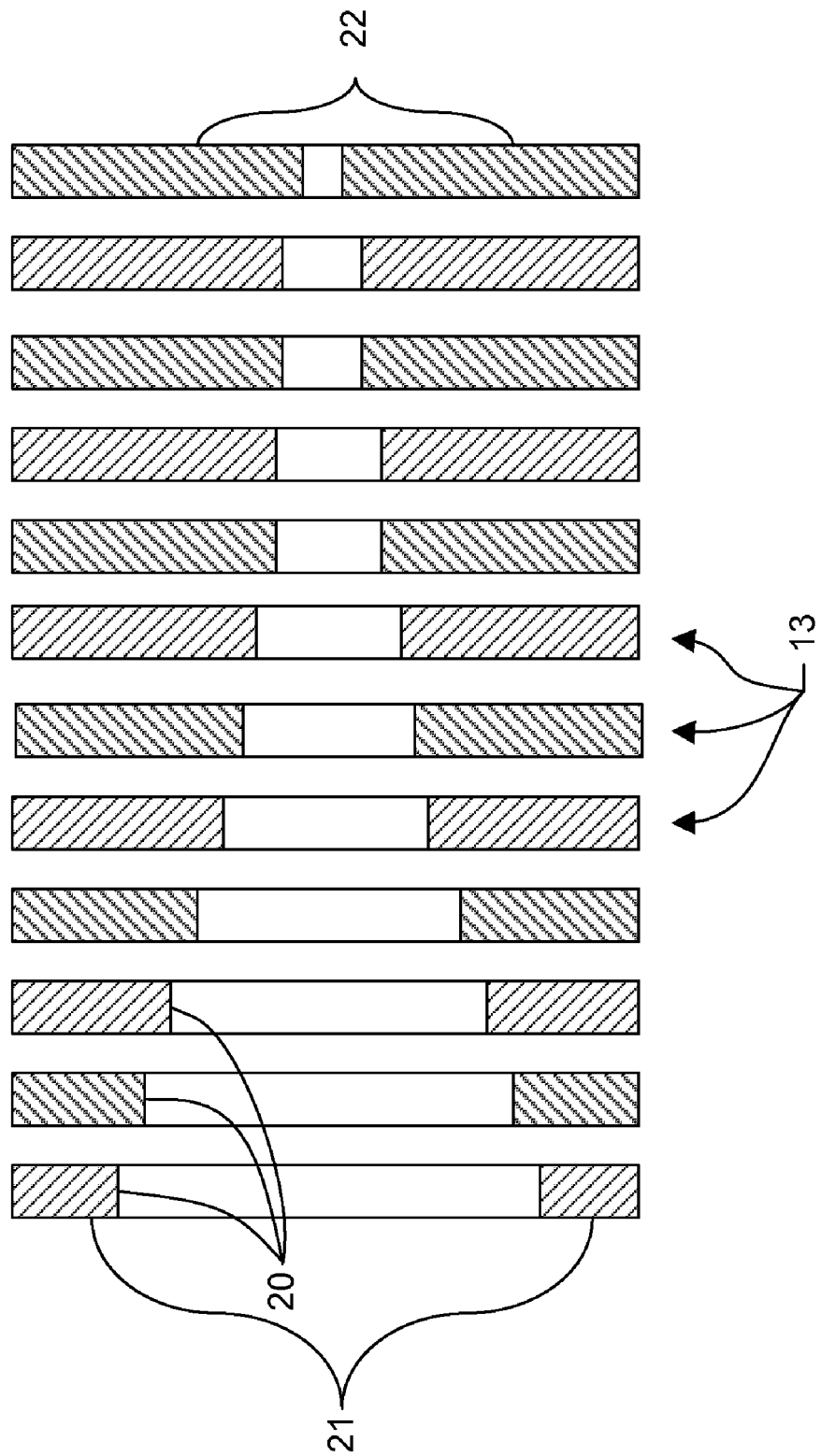
FIG. 2 depicts a prior art "ion funnel" guide according to Smith et al.

In one embodiment, a capillary, which might be capillary 7 as shown in FIG. 1, transmits ions and gas from an atmospheric pressure ion production means (not shown in FIG. 5) into chamber 171. Once the transmitted ions exit the end 34 of the capillary into first chamber 171, extended ion funnel 152, residing in first chamber 171, accepts the transmitted ions, while much of the gas introduced via the capillary is pumped away via pumping port 181 to maintain a desired pressure therein. Through the appropriate application of electric potentials as further discussed below, entrance focusing section 143 focuses the transmitted ions from exit end 34 of the capillary into mobility analysis section 145. Given that the pressure in chamber 171 is 2 mbar, the pressure in chamber 173 is 0.2 mbar, and that the aperture in electrode 155 is 2 mm in diameter, it is easy to determine that about 2 liters/second of gas are pumped through channel 141. Given the diameter of channel 141 is 8 mm, the average velocity of gas in the channel is about 20 m/s. This implies a Reynolds number of about 13—well within the laminar flow regime.

Ions transmitted through extended ion funnel 152 and the aperture of electrode 155 into second chamber 173 are collected by second ion funnel 191. Second ion funnel 191 focuses the ions and transmits them through a second pumping restriction into pumping chamber 175.

Preferably, multipole ion guide 193 resides in third chamber 175 and quadrupole analyzer 195 resides in fourth chamber 177. Ion guide 193 serves to guide ions through chamber 175 toward and through lens 194 whereas gas is pumped away via a pump (not shown) attached at port 183. Ions passing through lens 194 enter quadrupole analyzer 195. Quadrupole analyzer 195 consists of four rods equally spaced at a predetermined radius around a central axis. A radio frequency (RF)—e.g. a 1 MHz sine wave—potential is applied between the rods. The potential on adjacent rods is 180° out of phase. Rods on opposite sides of the axis of quadrupole 195 are electrically connected—i.e. the quadrupole is formed as two pairs of rods. Ions travel along the axis of quadrupole 195 and exit the quadrupole through the aperture in electrode 196. The RF potential applied between the rods will tend to confine the ions radially. When only RF is applied between the rods, substantially all ions will be transmitted through the quadrupole. Applying a DC as well as an RF potential between the pairs of rods will cause ions of only a limited mass range to be transmitted through quadrupole 195. Ions outside this mass range will be filtered away and will not reach the exit end.

Ions exiting quadrupole 195 via the aperture in electrode 196 will enter collision cell 199. Multipole 197 resides in collision cell 199. Multipole 197 may include any number of rods but in the preferred embodiment multipole 197 is a hexapole. An RF potential of, for example 800 Vpp at a frequency of 1.2 MHz confines the ions radially in the multipole. Collision cell 199 is maintained at an elevated pressure of a collision gas. For example, a pressure of $5\times10^{-3}$ mbar of Ar may be maintained by leaking Ar into cell 199 via a tube and regulating valve connected between a gas cylinder and the cell. Ions entering cell 199 will collide with the collision gas and thereby lose kinetic energy. The kinetic energy is converted in part into internal modes. If the potential difference between quadrupole 195 and collision cell 199 is sufficiently high, then the ions will be accelerated to a kinetic energy sufficient to result in collisionally activated dissociation (CAD) of the ions. Ions—either the original ions or fragment ions—are transmitted out of collision cell 199 via the aperture in electrode 198. Ions passing through lens 198 into fifth chamber 179 may subsequently be analyzed by any known type of mass analyzer (not shown) residing in chamber 179. The mass analyzer in chamber 179 may be any known type of mass analyzer including a time-of-flight mass analyzer, a quadrupole filter, a Paul trap, a quadrupole linear ion trap, an ion cyclotron resonance mass analyzer, or an orbitrap mass analyzer.

In alternate embodiments, other ion optics known in the prior art may be incorporated in the instrument of FIG. 5 so as to perform other reactions—e.g. electron transfer dissociation (ETD), infrared multiphoton dissociation (IRMPD), surface induced dissociation (SID), deuterium exchange reactions, or proton transfer reactions. In further alternate embodiments, other analyzers may be incorporated in the instrument of FIG. 5 so as to perform other experiments. For example, an additional ion mobility analyzer may be incorporated between collision cell 199 and the mass analyzer of chamber 179. Alternatively, a multitude of mass or mobility analyzers may be incorporated at any point in the instrument so as to perform any desired combination of mobility and mass analyses. In further alternate embodiments, more than one extended ion funnel may be used and these may reside in any desired chamber(s) in the instrument's vacuum system.

In experiments wherein CAD or other reactions are employed, reaction conditions may be varied during the experiment as a function of the mobility of the ions being released from extended ion funnel 152. In the preferred embodiment, during a mobility analysis in extended ion funnel 152, low mobility ions are released first and high mobility ions are released later in the analysis. Lower mobility ions will tend to have higher mass to charge (m/z) ratios. Also, higher m/z ions tend to require a higher collision energy to fragment. Thus, when lower mobility ions are released, the potential on collision cell 199 may be set for higher collision energies and when higher mobility ions are released from extended ion funnel 152, the collision cell may be set for lower collision energies.

Although the potentials applied to the components of the system shown in FIG. 5 may be varied widely, an example of the DC electric potentials that may be applied to each component in operating such a system in the analysis of positive ion are:

| | |
|---|---|
| capillary end 34 | 125 V |
| deflection electrode 239 | 130 V |
| segmented electrode 101 | 90 V |
| segmented electrode 136 | 20 V |
| lens element 155 | 19 V |
| second funnel 191 | 17 V |
| multipole 193 | 16 V |
| quadrupole 195 | 14 V |
| hexapole 199 | 10 V |
| electrode 198 | 0 V. |

Notice in FIG. 5, that capillary end 34 is oriented orthogonal to the axis of the funnel—rather than axially as in many prior art systems. Gas flowing out of capillary end 34 will have a directed forward motion that will tend to carry the gas past the funnel along path 172 and into pumping port 181. Ions are deflected out of the gas stream on path 172 and into the funnel entrance by a potential applied to electrode 239. Ions and a fraction of the gas from capillary end 34 pass into extended funnel 152 and channel 141. In alternate embodiments, capillary end 34 may be replaced by an orifice or other similar structure connecting by gas flow the ion production region with chamber 171.

As described in co-pending application Ser. No. 11/219, 639, electrode 239 can also be used as a sample carrier for a Matrix-Assisted Laser Desorption/Ionization (MALDI) ion production means. In this embodiment, MALDI samples are applied to the surface of electrode 239 according to well known prior art methods. Window 242 is incorporated into the wall of chamber 171 such that laser beam 241 from a laser positioned outside the vacuum system may be focused onto the surface of electrode 239 such that the sample thereon is desorbed and ionized. Ions can be introduced from an electrospray ion production means via capillary end 34 while simultaneously producing MALDI ions from samples on electrode 239. Though not shown, more than two ion production means can be used in this manner either consecutively or simultaneously to introduce ions into extended ion funnel 152.

Each segmented electrode 101-136 in ion funnel 152 consists of four conducting elements a-d as depicted in FIG. 4A. Within any given segmented electrode 101-136, element a is in electrical contact with element c and element b is in electrical contact with element d. That is, element 101a is electrically connected to element 101c, element 101b is electrically connected to element 101d, element 102a is electrically connected to element 102c, and so forth.

Both RF and DC potentials are applied to the segments of each electrode 101-136. Within a segmented electrode, the same DC potential is applied to all segments. For example, all elements 101a-101d have the same 120 V DC potential. The RF potential is applied between segments of each electrode. For example, the RF potential applied to extended funnel 152 may be a 1.2 MHz sine wave having an amplitude of 200 Vpp. A first such RF potential may be applied to segments 101a and 101c whereas a second identical RF potential 180° out of phase with the first is applied to segments 101b and 101d. The same RF potential of the same frequency and amplitude is applied to every segmented electrode 101-136; however, the RF phase is varied as a function of electrode position. Within focusing sections 143 and 147 the phase of the applied RF potentials is varied such that the phase of the applied RF on adjacent electrodes is 180° out of phase both within a segmented electrode and along axis 153 of funnel 152. For example, if the phase of the RF on electrode 102a is 0° then the phase of the RF on electrodes 102b and 102c as well as on electrodes 105a-108a will be 180°, whereas the phase of the RF on electrodes 101a, 103a, and 104a will all be 0°. In alternate embodiments, the RF amplitude applied to some of electrodes 101-136 differs from that applied to others. In alternate embodiments, the RF amplitude applied to the electrodes of section 145 is independent from that applied to sections 143 and 147. In alternate embodiments, the RF amplitude applied to the electrodes of section 145 may be varied over time during the course of an ion mobility analysis.

Figure 6:
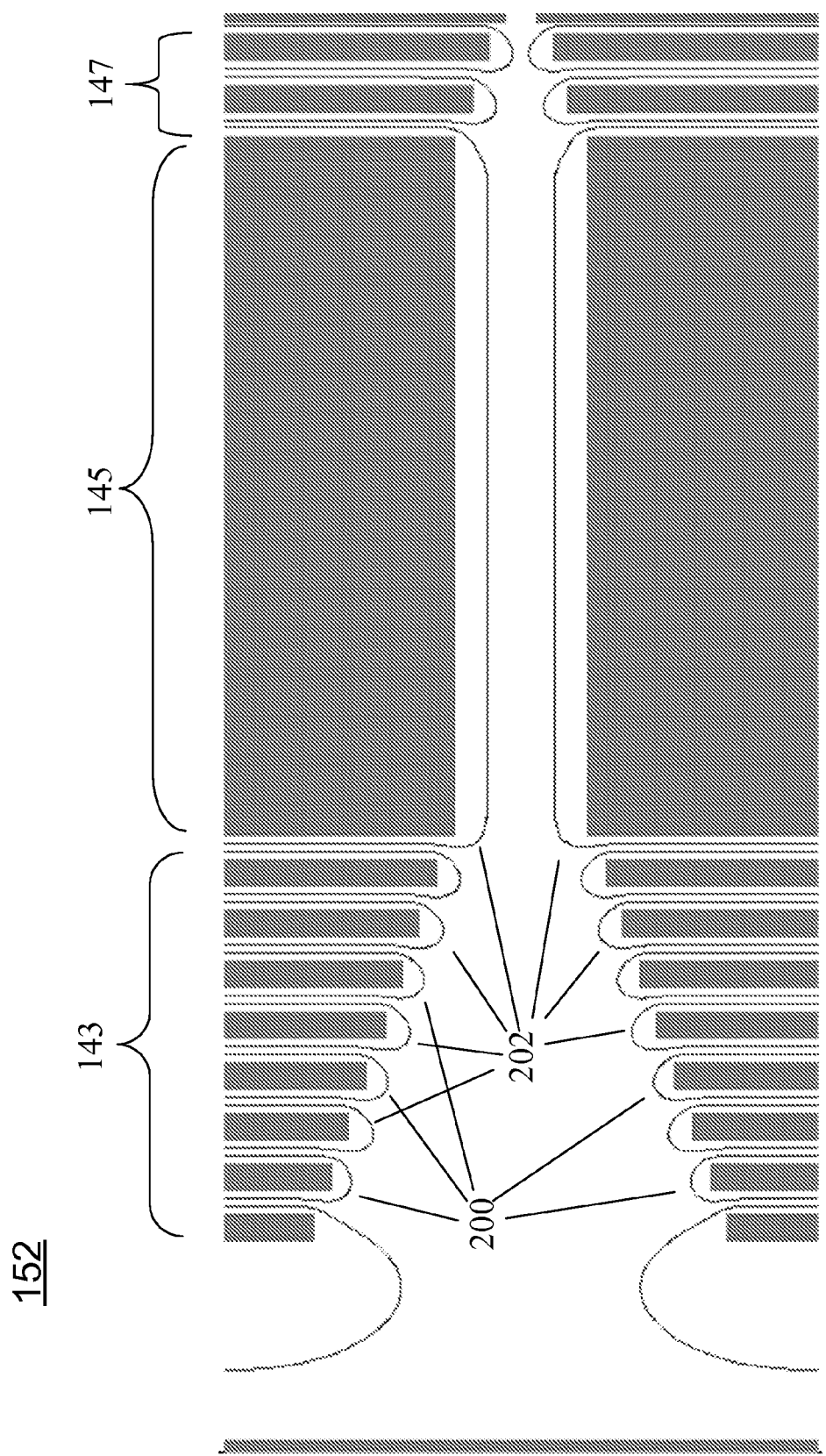
FIG. 6 depicts an approximation of the RF equipotential lines formed in funnel 152 when operated according to the preferred method.

Because the RF phase alternates along axis 153, the RF electric field in focusing sections 143 and 147 is dipolar as represented in FIG. 6. FIG. 6 depicts an approximation of the RF equipotential lines formed in funnel 152 when operated according to the preferred method. Equipotential lines 200 and 202 were approximated at an instant when the potentials on segmented electrodes 101-136 were +/−100V—i.e. the potential on electrodes 101a-104a, 109a-134a, and 136a was +100V whereas that on electrodes 105a-108a and 135a was −100V. Equipotential lines 200 were formed at a −30V equipotential whereas lines 202 were formed at a +30V equipotential. By visual inspection, the field formed in the focusing sections 143 and 147 is clearly dipolar in nature and confined to the region near the electrodes.

Figure 7:
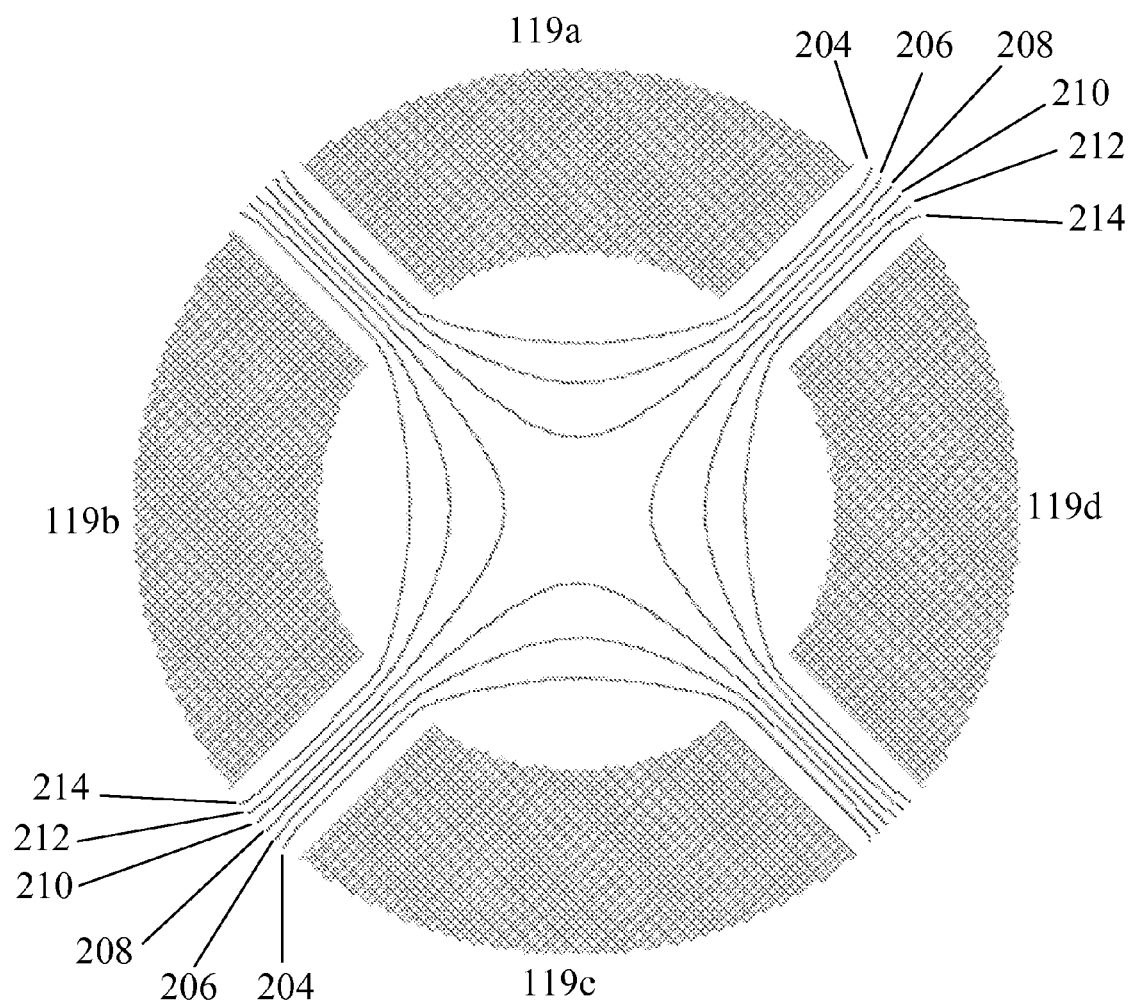
FIG. 7 is a cross sectional view at segmented electrode 119 showing simulated equipotential lines representing the RF field in channel 141.

In analysis section 145, the RF electric field has more of a quadrupolar nature. Importantly, in analysis section 145, the phase of the applied RF does not vary along the axis. That is, electrodes 109a-134a all have the same phase RF applied to them. FIG. 7 depicts the result of a simulation of the RF field in analysis section 145. FIG. 7 is a cross sectional view at segmented electrode 119. For the purpose of the simulation, the potential on electrodes 119a and 119c was taken to be +100V whereas the potential on electrodes 119b and 119d was assumed to be −100V. Lines 204, 206, 208, 210, 212, and 214 are the equipotential lines formed at 50V, 30V, 10V, −10V, −30V, and −50V respectively. The +/−10V equipotential lines clearly show a quadrupolar field form. That is, near axis 153 within analysis section 145, the RF field takes the form $A(x^2-y^2)+B$, where A and B are constants and x and y are coordinates in a Cartesian system orthogonal to and originating on axis 153. The quadrupolar RF field in analysis section 145 focuses ions towards axis 153 more effectively than the dipolar field that would be formed if the phase of the RF potential alternated along the axis as in focusing section 143. Moreover, as can be inferred from the RF equipotential lines in FIG. 6, the quadrupolar RF field in analysis section 145 has substantially no component along axis 153. In contrast, the dipolar RF field in focusing section 143 clearly has an axial component. In alternate embodiments segmented electrodes 101-136 may be formed of any number of electrode segments—i.e. a single segment, two segments, six segments, etc. If segmented electrodes 109-134 of section 145 are formed of a single segment, then the RF potential must be applied between adjacent electrodes. In such a case, the phase of the RF applied to the electrodes is shifted by 180° between adjacent electrodes rather than maintaining the same phase throughout section 145. Clearly, the order of the RF field near axis 153 will be governed by the number of segments used to form electrodes 101-136. That is, if six segments are used, the RF field will be hexapolar, if eight segments are used, the RF field will be octapolar, etc. While higher order RF fields may be used, they will not be as effective at focusing the ions to axis 153.

The focusing of ions toward axis 153 by the RF field in analysis section is important in the mobility analysis of ions according to the present invention. In order to obtain the best possible mobility resolution, the gas flow experienced by the ions must be as uniform as possible. Under no-slip boundary conditions, a laminar gas flow has a parabolic velocity profile. In order for the every ion to experience the same gas velocity they should ideally be located at the same radial distance from axis 153. Furthermore, because the flow has a parabolic velocity profile, the change in velocity as a function of radial distance from axis 153 is minimal near axis 153. Also, while electrodes 101-136 are substantially cylindrically symmetric, slots 151 break the cylindrical symmetry. Thus, close to the slots, the gas flow will not be cylindrically symmetric and ions there would experience a non-uniform gas flow. Close to axis 153, the asymmetry in the gas flow caused by slots 151 is minimized. So, for both these reasons, focusing the ions to near axis 153 will yield the best possible mobility resolution at the highest possible analysis speed.

The absence of a quadrupolar RF field component along axis 153 in analysis section 145 is also important to the effectiveness of the mobility analysis in that an axial RF field component would result in an axial pseudopotential that would have an influence on the ions according to their mass-to-charge (m/z) ratios rather than their mobilities. In the extended ion funnel according to the present invention, there are 0.1 mm gaps between adjacent electrodes 109-134. These gaps will weaken the quadrupolar RF field in the vicinity of the gaps. However, at distances from the gaps much larger than the gaps themselves, the weakening in the RF field is not noticeable. Thus, focusing ions towards axis 153 and thereby away from the gaps will tend to improve the uniformity of the RF field experienced by the ions.

In a similar manner, the uniformity of the axial DC electric field in analysis section 145 is also important to the performance of the present invention. In operation according to the preferred method, the DC electric field strength varies as a function of position along axis 153. However, at some position in analysis section 145 the field strength reaches a maximum so as to form a barrier which ions must overcome in order to reach exit end 167 of extended funnel 152. Near this position of maximum field strength, the uniformity of the DC field is most important in that this is the point at which ions are selected on the basis of their mobility. Most importantly the DC field should be cylindrically symmetric. Due to the presence of slots 151 as discussed above, the DC field will be most uniform near axis 153. It is worthwhile to note that a slightly weakening DC axial field gradient at larger radial distances from axis 153 will have a minimal effect on the mobility analysis because the gas flow pushing ions against the electric field will drop off according to the parabolic flow profile reaching a velocity of zero at the radius of channel 141. As the velocity drops with radial position, the force on the ions associated with the gas flow will drop and ions at these radial positions will be pushed backwards against the gas flow even by a slightly weakened DC axial field. Ions having mobilities just low enough to pass the above mentioned DC field barrier will do so only in the region of the gas flow having the highest velocity—i.e. near axis 153.

Notice, in FIGS. 4A and 6 that all segmented electrodes have the same form—i.e. concave quadrupolar. Notice also that the RF potential applied to segmented electrode 109 is 180° out of phase with respect to that applied to segmented electrode 108; however, it is in phase with all electrodes 110-124. In this way a smooth transition is made from focusing section 143 to analysis section 145. The smooth transition is visibly evident in the equipotential lines of FIG. 6. Similarly, segmented electrode 134 is used to create a smooth transition from analysis section 145 to focusing section 147.

As described above, a conventional drift mobility analyzer includes a drift cell wherein a carrier gas is essentially at rest. Ions are introduced at an entrance end of the drift cell and allowed to move, under the influence of a homogeneous DC electric field, to the exit end of the drift cell. The ions move through the carrier gas with a velocity, v, which is proportional to the mobility of the ion and the strength of the electric field. The time required for the ions to move through the cell naturally equals the length, l, of the cell divided by the velocity of the ion. To a point, the mobility resolution of the cell improves as the cell is lengthened.

In contrast, the parallel flow ion mobility analyzer according to Zeleny [J. Zeleny, *Philos. Mag.* 46, 120(1898)] uses a drift cell wherein the carrier gas is moving with a speed, u. The carrier gas moves in a direction opposing the motion of the ions in the electric field. The time required for the ions to pass through the cell is $l/(v-u)$. In effect, the path of the ion through the carrier gas is lengthened and the resolution can thereby be improved. If the speed of the gas is increased so as to be equal to the speed of the ion through the gas, then the ion will not move relative to the cell. In this limit, the mobility resolution of the device can theoretically be infinite.

In the parallel flow ion mobility analyzer according to the present invention, ions are trapped in channel 141 by the combination of an RF field that confines the ions radially about axis 153, an axial DC field that prevents the ions from moving towards exit 167, and a gas flow that prevents ions from moving out of the entrance end of channel 141. As in the parallel flow analyzer of Zeleny, the carrier gas flow is counter to the motion of the ions in the gas under the influence of the electric field. After trapping ions, the strength of the axial DC field is gradually reduced so that the velocity of the ions relative to the gas is reduced and ions of successively higher mobilities exit the analyzer.

Figure 12:
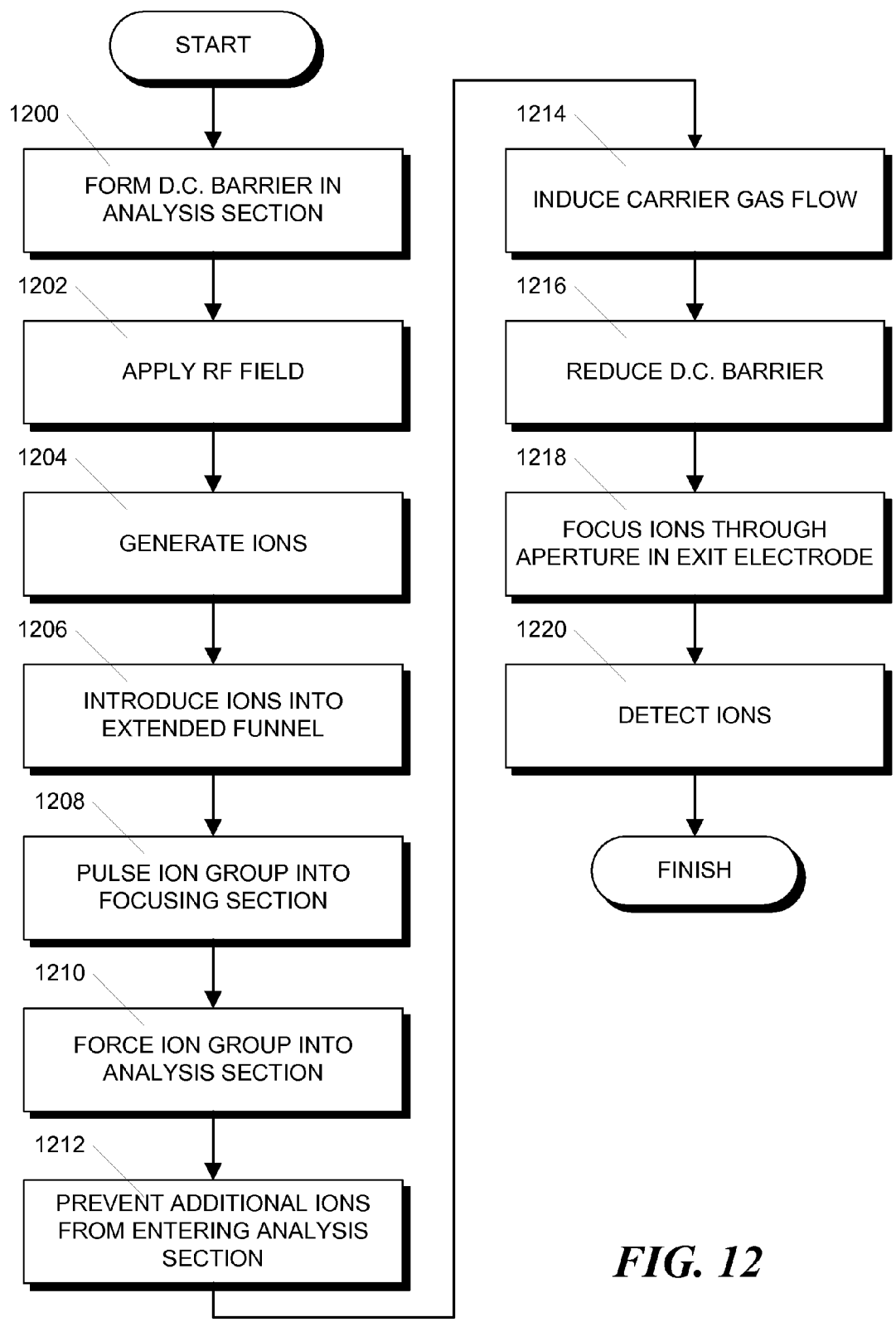
FIG. 12 is a flowchart showing the steps in an illustrative process for operating the mass spectrometer of FIG. 5

One preferred method of operation according to the present invention is shown in FIG. 12 and consists of the steps of:

a) forming a DC barrier in analysis section 145 (step 1200);

b) applying an RF field for focusing ions towards axis 153 (step 1202);

c) generating ions in an ion source (step 1204);

d) introducing ions in a carrier gas into extended funnel 152 (step 1206);

e) pulsing a group of ions into focusing section 143 by applying a pulsed potential to deflection electrode 239 (step 1208);

f) forcing said group of ions into analysis section 145 by applying a first set of DC potentials to the electrodes of focusing section 143 (step 1210);

g) preventing additional ions from entering analysis section 145 by applying a second set of DC potentials to deflection electrode 239 and the electrodes of focusing section 143 (step 1212);

h) inducing a carrier gas flow through channel 141 using a pump downstream from the exit end of funnel 152 (step 1214);

i) gradually reducing said DC barrier in analysis section 145 so as to allow said carrier gas flow to push ions from said group of ions over the DC barrier in order of the ions' mobilities (step 1216);

j) focusing ions through the aperture in exit electrode 155 (step 1218); and k) detecting ions that have been ejected from analysis section 145 (step 1220).

Figure 8:
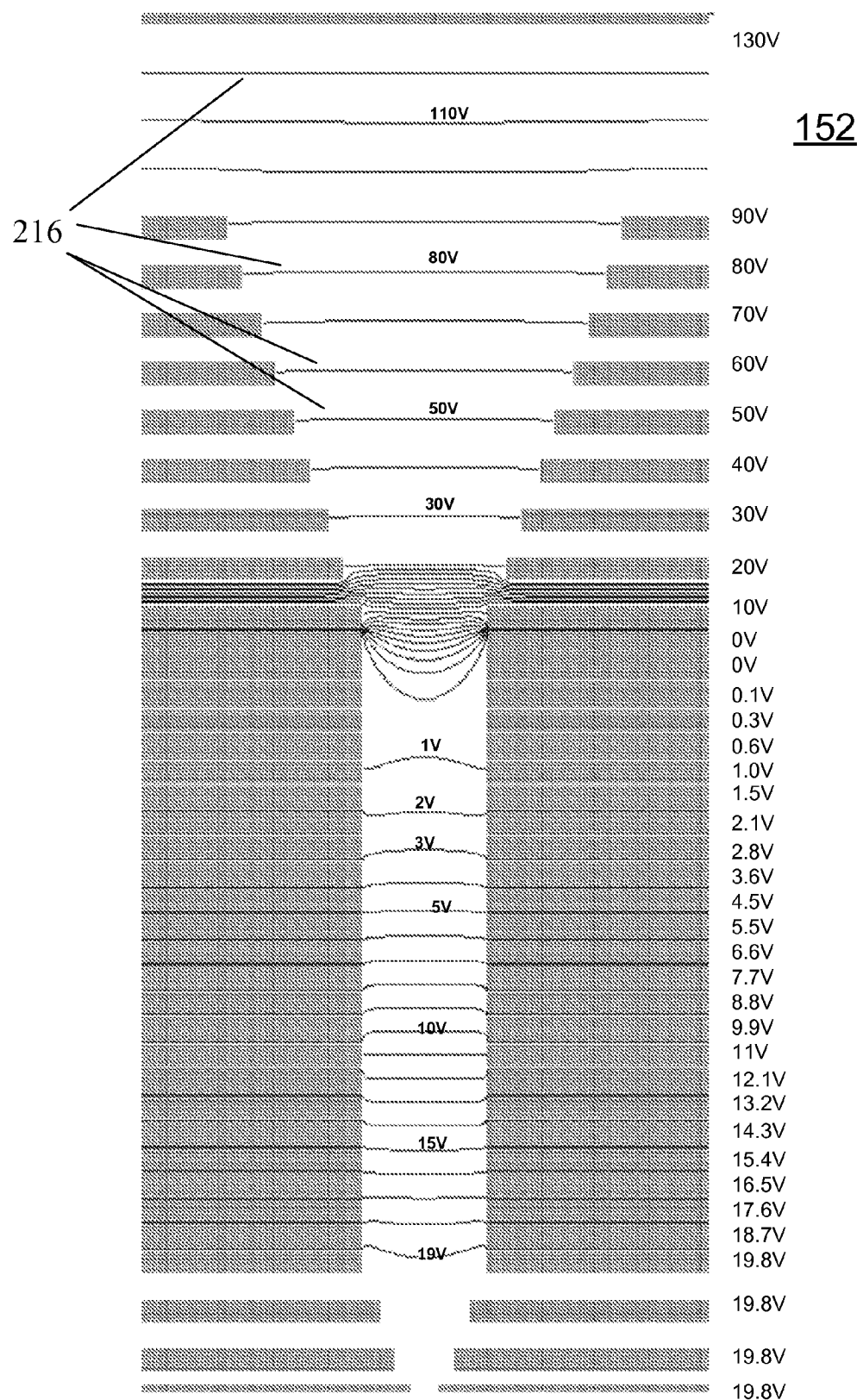
FIG. 8 depicts the results of a simulation of the DC electric field in funnel 152 during the injection of a group of ions into sections 143 and 145.

FIG. 8 depicts the results of a simulation of the DC electric field in funnel 152 during the injection of a group of ions into sections 143 and 145 (steps "e" and "f" above). In FIG. 8 the DC potentials applied to the electrodes of the funnel are listed immediately above the electrode to which the potential is applied. The potentials shown are used during the analysis of positively charged ions. Any combination of RF and DC power supplies, devices, or components may be used to apply the desired RF and DC potentials to the electrodes of funnel 152. In the preferred embodiment, a network of resistors and capacitors is used in conjunction with RF and DC power supplies and switches (steps "a" and "b") to apply the needed potentials to electrodes 101-136, 155 and 239.

Analyte ions may be formed (step "c") by any ion production method including atmospheric pressure chemical ionization (APCI), desorption electrospray ionization (DESI), atmospheric pressure photoionization (APPI), etc., however, as an example, the ions are formed by electrospray ionization. Any type of gas may be used as drying gas 27 (FIG. 1). In the electrospray process, the ions are formed in drying gas 27 at near atmospheric pressure. Some fraction of drying gas 27 and the ions in it flows into capillary 7 by the action of the vacuum in pumping region 171. In the preferred embodiment, the same gas acts as the carrier gas (step "d") with the ions already in it when it exits capillary end 34. In alternate embodiments, the carrier gas may be a different type of gas than drying gas 27. In such alternate embodiments, drying gas 27 is pumped away and replaced by a means (not shown) between the ion source and capillary end 34. Such means may include, for example, pumps, gas inlets, semi-permeable membranes and the like. Drying gas 27 and the carrier gas may be any type of gas including $N_2$, Ar, He, $CO_2$, $O_2$, $H_2O$, $CH_4$ or mixtures thereof.

In FIG. 8, equipotential lines 216 show a uniform field is formed in focusing section 143 and this field pushes the ions towards analysis section 145. Ions exiting capillary end 34 are pushed by the electric field out of directed gas flow 172 through focusing section 143 and into analysis section 145.

In analysis section 145 the DC electric field pushes ions away from exit end 167. The RF field applied to electrodes 109-134 will tend to confine the ions radially near axis 153. The flow of gas pushes the ions towards exit end 167. Thus, ions within a mobility range become trapped. Assuming a flow velocity of 20 m/s, and an axial DC field strength of 6.4 V/cm, all ions having reduced mobilities above about 0.62 will become trapped. At a pressure of 2 mbar, a field strength of 6.4 V/cm corresponds to a ratio of field strength to gas number density of about 23 Townsends (Td). At field strengths substantially above 20 Td, the mobilities of some ions may be no longer independent of the field strength. The point at which the ion mobilities are no longer independent of the axial DC field strength is referred to as the "low field limit". The low field limit is not well defined; however, operating far above the low field limit may complicate mobility measurements.

In order to measure lower mobility ions without operating outside of the low field limit, the flow velocity of the carrier gas in channel 141 may be reduced. Any method of reducing the carrier gas flow velocity may be used; however, as an example, the pressure in pumping region 173 may be increased by throttling the pump at port 182. Alternatively, the pressure in region 173 may be increased by introducing gas into that region via a needle valve. Alternatively, one or more of gaskets 157 may be partially or completely removed so as to allow some gas to pass between electrodes 134-136 in order to reach exit 167. This will effectively increase the pressure in section 147 and reduce the amount of gas that passes through channel 141. Alternatively, the aperture in electrode 155 may be made adjustable so that more or less gas flows through channel 141 per unit time if the aperture is adjusted to a larger or smaller diameter.

Reducing the gas flow velocity through channel 141 will tend to reduce the resolution of the present invention. In order increase the resolution, the flow velocity may be increased. The flow velocity may be increased by increasing the pressure at the entrance of section 145 or decreasing the pressure at the exit of section 145 by similar methods as described above.

In alternate embodiments gaskets 157 may be removed and section 147 may reside in a separate pumping chamber from sections 143 and 145. In such an alternate embodiment, a gas tight seal is made between electrode 134 and chamber 180. An additional pumping port is used to pump the region thus formed. By throttling the pump at pumping port 181 and increasing the pumping on section 147, the velocity of the gas flow in channel 141 may be increased. By increasing the pumping at port 181, reducing the pumping on section 147 and/or introducing gas into section 147 via a valve, the velocity of the gas flow in channel 141 may be reduced or even reversed.

In some cases it may also be useful to work outside of the low field limit. For example, under a given set of conditions, two types of ions may have the same ion mobility within the low field limit. In a mobility analysis within the low field limit these two types of ions would be indistinguishable by their mobilities alone. However, as the gas flow velocity—and therefore field strength—is increased above the low field limit, the mobilities of the ions will change as a function of field strength. If the mobility of the ions of one type changes differently than the mobility of the ions of the other—i.e. if the ions have different a values—then they may become distinguishable from one another. To work outside the low field limit, the flow velocity of the gas in channel 141 is increased such that the axial DC field strength needed to prevent the ions from escaping from section 145 is above the low field limit.

Figure 9:
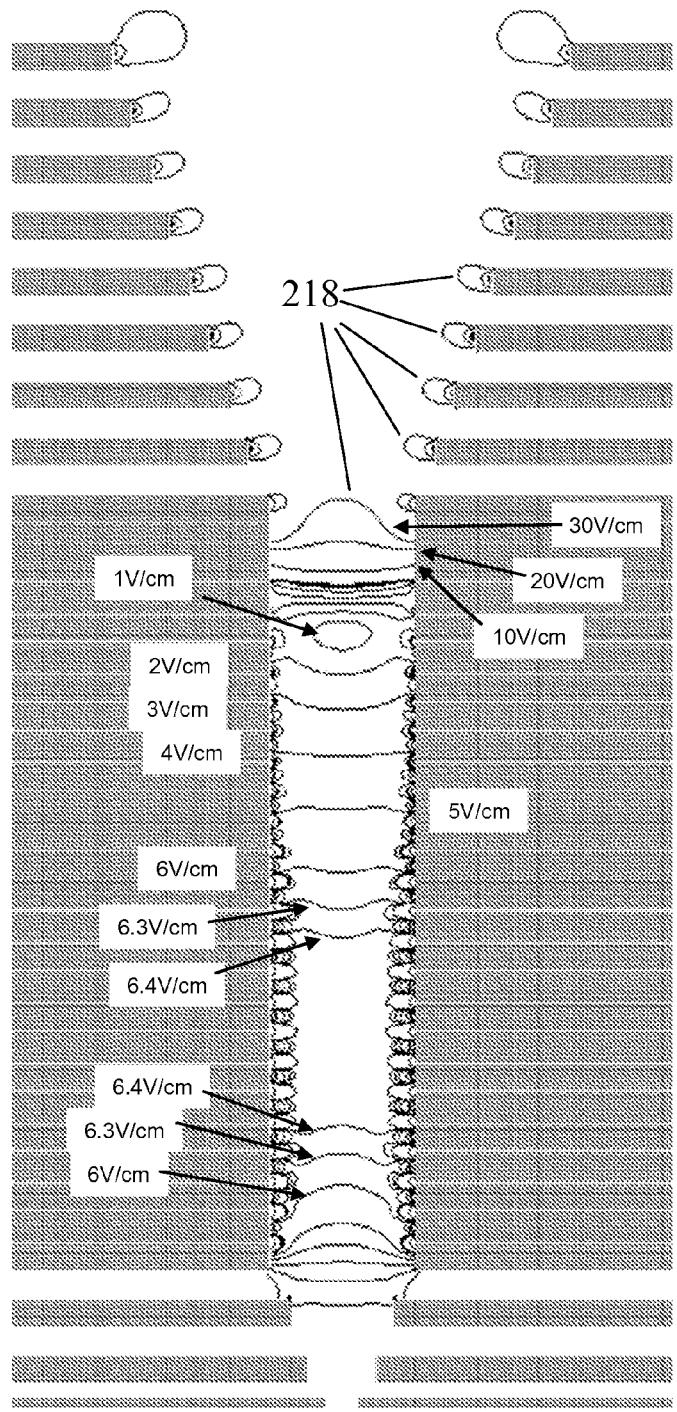
FIG. 9 depicts the equigradient lines associated with the field simulated in FIG. 8.

FIG. 9 depicts the equigradient lines associated with the field simulated in FIG. 8. Some of equigradient lines 218 are labeled according to their field strength in Volts per centimeter. As shown, the DC electric field strength is not constant along axis 153. Rather, near the entrance end of section 145, the field strength is low whereas near the exit end the field strength is high. Near electrode 127 the DC electric field strength is highest. Ions trapped in section 145 will therefore become distributed over a range of positions between electrode 113 where the field strength is lowest to electrode 127.

Ions having high mobilities will be trapped about axis 153 near electrode 113 whereas ions of the lowest mobilities will be trapped about axis 153 near electrode 127. Ions of intermediate mobilities will be distributed along axis 153 between electrodes 113 and 127 according to their mobilities the highest mobility ions nearest electrode 113 and the lowest near electrode 127. In step "i" when the DC barrier is gradually reduced, all the potentials on electrodes 112-136 and 155 are reduced in proportion to their original blocking DC potentials. Thus, as the DC barrier is lowered, the gas flow will push the lowest mobility ions over the barrier. Simultaneously, the DC gradient in the rest of analysis section 145 is reduced and ions remaining in this section are redistributed closer to the barrier.

Notice in FIG. 8 that near electrode 127 the equipotential lines are substantially straight and parallel to one another. This implies that the axial DC field is uniform in this region where the low mobility cutoff occurs. The uniform field strength is also reflected in the equigradient lines of FIG. 9. In FIG. 9 two 6.4V/cm equigradient lines are shown—one adjacent to electrode 123 and the other adjacent to electrode 130. Between these two 6.4V/cm lines the strength of the axial DC field varies by less than ~0.06V/cm—i.e. ~1%.

In step "g" above—preventing additional ions from entering section 145—the ions may be prevented from entering section 145 by changing any or all of the potentials on funnel 152, however, as an example, the potential on electrode 239 is changed to −130 V. The positive ions are thereby attracted to and collide with electrode 239. In steps "e" and "f" electrode 239 is pulsed momentarily to +130V (assuming the analysis of positively charge ions) and then returned to −130V for all other steps. In alternate embodiments, ions may be prevented from entering section 145 by appropriately changing any potential on any electrode between the ion production region and section 145. In further alternate embodiments, the production of ions may be interrupted or the passage of ions may be blocked by a physical barrier—i.e. a shutter. The duration of the pulse on electrode 239 may vary widely; however, the number of ions captured in analysis section 145 during the pulse should be low enough that Coulomb effects will be unimportant. The charge carried by the analyte ions that are trapped in section 145 during steps "e" and "f" will create a field of its own. The strength of the field created by the charge on the ions should be substantially less than the field created via electrodes 109-136. The strength, Ex, of the axial field associated with the ions can be approximated as:

$$Ex = \frac{Q}{400 \cdot \pi \cdot \varepsilon \cdot l}\left(\frac{1}{l_o} - \frac{1}{l+l_o}\right) \quad (1)$$

where Q is the total charge of the trapped ions, l is the length of the line of charge, and $l_o$ is the distance between the line of charge and the ion under analysis. Using equation 1 it can be shown that about $10^6$ charges can be trapped before Coulomb effects become important. Thus, if an ion beam of $10^8$ charges is produced at the exit of capillary 34 and these charges are captured with a 10% efficiency, then steps "e" and "f"—and the pulse on electrode 239—should have a duration of 100 ms in order to fill analysis section 145.

Overfilling section 145 with ions will result in Coulombic repulsion between the ions. That is, if the field created by the charge on the ions is comparable in strength to the electric field created via the electrodes, then the field of the ions will substantially influence the performance of funnel 152. Coulombic effects may reduce the mobility resolution of the funnel and will shift the apparent mobility of the ions. That is, when funnel 152 contains a large number of ions the field produced by the ions will tend to counter the axial DC field generated by the electrodes. This will shift cause ions to overcome the axial DC field at higher field strengths than would otherwise be possible. Because the ions will be able to exit section 145 at higher apparent DC field strengths, the ions will appear to have lower mobilities than they otherwise would. This effectively shifts the mobility calibration toward lower mobilities when analysis section 145 is overfilled. Thus, in one alternate method, the ion current is monitored and the filling time of section 145 is varied according to the level of ion current so that the number of ions trapped in section 145 is nearly the same from one mobility analysis to another.

If the axial DC field in section 145 were eliminated—i.e. if the DC potential difference across analysis section 145 is zero volts—then the minimum time required for ions to move from the entrance of section 141 to its exit will equal the length of channel 141 divided by the carrier gas velocity. A wide range of carrier gas velocities might be used, however, as an example, the carrier gas velocity in channel 141 may be 20 m/s. A wide range of channel lengths might also be used, however, in the preferred embodiment, channel 141 is 44 mm long. Thus, in the preferred embodiment, the minimum time for ions to pass through channel 141 is 0.044/20=0.0022 s. The minimum time for a mobility analysis according to the above method is about 2 ms. For practical purposes, a much longer time is required to separate the ions under the influence of an opposing axial DC field. In the preferred embodiment step "i" the gradual reduction of the DC barrier is carried out over a period of, for example, 100 ms. Notice this time for a mobility analysis is the same as the time required in steps "e" and "f" to fill analysis section 145. Accordingly, this method has a 50% duty cycle. That is, 50% of the time is spent accumulating ions. The 50% of the ions produced during the analysis step "i" are lost. In alternate methods, steps "e" and "f" and step "i" may have any duration.

Another consideration in the duration of analysis step "i" is the desired resolution. The resolution of a mobility spectrum can be defined as the mobility of a given peak divided by its width. As detailed in the technical literature, the theoretical upper limit of the resolution, R, for parallel mobility analyzer is given by:

$$R=[qE(l+ut)/2kT]^{0.5} \quad (2)$$

where q is the charge on the ion, E is the electric field strength, t is the drift time, k is Boltzmann's constant, and T is the temperature of the carrier gas. In the analyzer according to the present invention, the length, l, of channel 141 can be neglected. Thus, key factors determining the resolution are the electric field strength, the velocity of the gas, and the time of the analysis. As applied to the present invention, E should be interpreted as the field strength at which a given type of ion overcomes the DC barrier. It is clear from equation 2 that a longer analysis time—i.e. a slower rate of decrease in the DC barrier—will yield a higher resolution.

As long as the analyzer is operated in the low field limit, the mobility of the ions can be calculated from the DC barrier field strength as:

$$K=u/E \quad (3)$$

where K is the ion mobility, u is the velocity of the gas in channel 141, and E is the field strength of the axial DC barrier when the ion overcomes the barrier and exits the analyzer section 145.

Alternatively, because u and E may not be known with sufficient precision, the instrument may be calibrated using calibrants. In such a case, one or more ions having known mobilities in the selected carrier gas are mobility analyzed as described above. The axial DC potentials at which the calibrant ions are ejected from channel 141 are measured. A best fit of the equation:

$$K = a_1/V + a_0 \tag{4}$$

to the calibrant data is then made. In equation 4, "V" is the axial DC potential and "$a_1$" and "$a_0$" are constants. Higher order calibration equations including, for example, the terms "$a_2/V^2$", "$a_3/V^3$", might also be used, however, more calibrant species will be required.

An alternate method of operation according to the present invention consists of the steps of:

a) forming a DC barrier in analysis section 145;
b) applying an RF field for focusing ions towards axis 153;
c) generating ions in an ion source;
d) introducing ions in a carrier gas into extended funnel 152;
e) accumulating a group of ions into focusing section 143 by applying a first set of DC potentials to the electrodes of focusing section 143 and deflection electrode 239;
f) transferring said group of ions into analysis section 145 by applying a second set of DC potentials to the electrodes of focusing section 143;
g) inducing a carrier gas flow through channel 141 using a pump downstream from the exit end of funnel 152;
h) accumulating a second group of ions into focusing section 143 by applying the first set of DC potentials to the electrodes of focusing section 143 and deflection electrode 239;
i) simultaneous with step "h", gradually reducing said DC barrier in analysis section 145 so as to allow said carrier gas flow to push ions from said group of ions over the DC barrier in order of the ions' mobilities;
j) focusing ions through the aperture in exit electrode 155; and
k) detecting ions that have been ejected from analysis section 145.

Figure 10:
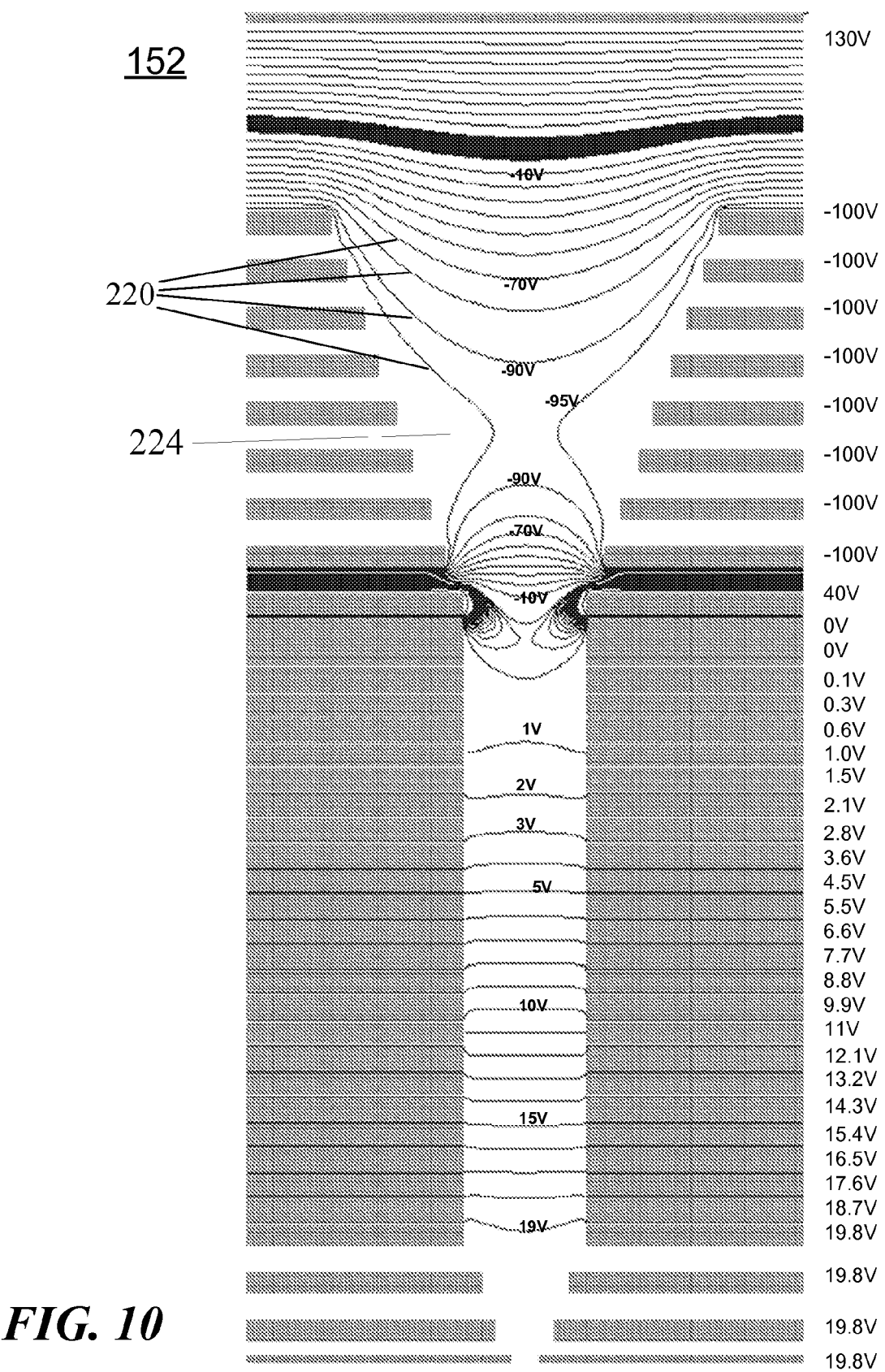
FIG. 10 depicts the results of a simulation of the DC electric field in funnel 152 during the accumulation of a group of ions into section 143.

FIG. 10 depicts the results of a simulation of the DC electric field in funnel 152 during the accumulation of a group of ions into section 143 (steps "e" and "h" above). In FIG. 10 the DC potentials applied to the electrodes of the funnel are listed immediately above the electrode to which the potential is applied. The potentials shown are used during the analysis of positively charged ions. Equipotential lines 220 show that the DC field formed in focusing section 143 pushes the ions exiting capillary end 34 towards the middle of focusing section 143. Ions exiting capillary end 34 are pushed by the electric field out of directed gas flow 172 towards the middle of focusing section 143. The negative potential on electrodes 101-108 attracts the ions whereas the positive potentials on deflection electrode 239 and segmented electrode 109 repel the positive ions. The RF potential on electrodes 101-109 radially confines the ions so that the ions are accumulated in torus shaped region 224.

Figure 11:
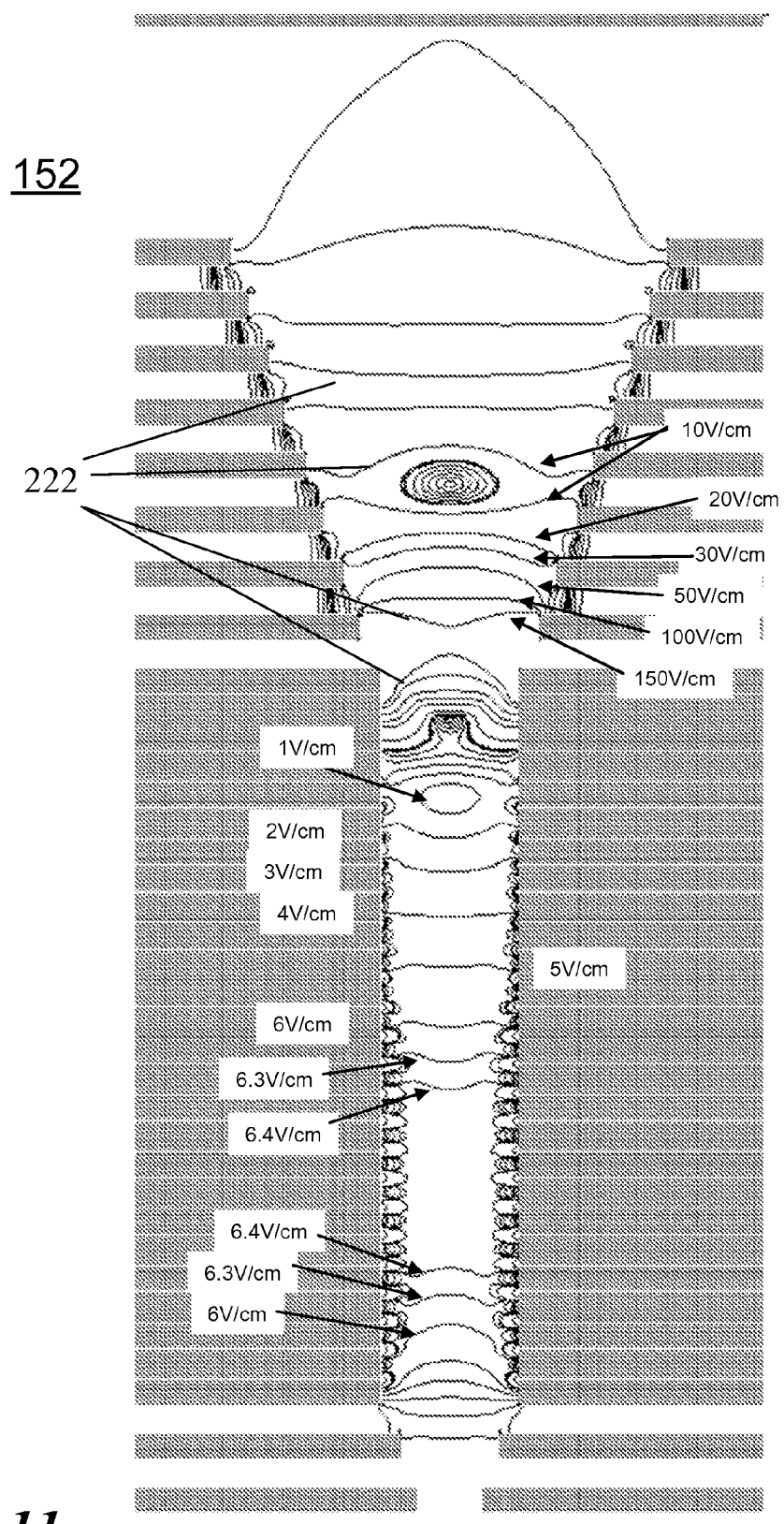
FIG. 11 depicts the equigradient lines associated with the field simulated in FIG. 10.

Notice in FIGS. 8 and 10 that changing the DC potentials on segmented electrodes 101-109 has little effect on the field, and therefore the equipotential lines, in analysis region 145. FIG. 11 depicts the equigradient lines associated with the field simulated in FIG. 10. Some of equigradient lines 222 are labeled according to their field strength in Volts per centimeter. Notice in FIGS. 9 and 11 that changing the DC potentials on segmented electrodes 101-109 also has little effect on the axial DC field strength in section 145. The implication is that ions may be accumulated in focusing section 143 while simultaneously analyzing ions in analysis section 145.

Once enough ions have been accumulated in section 143, the ions may be transferred to analysis section 145 (step "f") by momentarily pulsing the potentials on electrodes 101-109 to the DC potentials shown in FIG. 8. The potentials on electrodes 101-109 may be pulsed to those shown in FIG. 8 for a period of, for example, 1 ms such that all ions are pushed out of section 143 into section 145. After this 1 ms pulse, the potentials on electrodes 101-109 are returned to the potentials shown in FIG. 10. A second group of ions may then be accumulated in section 143 (step "h") while simultaneously analyzing the first group of ions for their mobilities in section 145 (step "i").

As mentioned above, any known source of ions may be used with the present invention. The two methods described above are intended for use with continuous sources such as ESI, APCI, DESI, APPI, etc. However, the present invention may also be used with any discontinuous or pulsed ion source. As mentioned with respect to FIG. 5, deflection electrode 239 may be used as a sample carrier for MALDI. Pulsed laser light 241 from a laser external to the vacuum system can pass through window 242 and desorption and ionization of the sample on electrode 239. As the laser light is pulsed, the ions will be produced from the MALDI sample in a pulsed manner as well. Given potentials on electrodes 101-136 and 239 similar to those listed in FIG. 8, ions produced from the MALDI sample will be accelerated into focusing section 143 and analysis section 145. Depending on conditions, a single laser shot may not result in the desired number of ions being captured in section 145. Several laser shots may be used to produce analyte ions before the mobility analysis in section 145 begins. The gas flow from capillary end 34 may be maintained as described above such that the velocity of the carrier gas in channel 141 is the same as described above. Alternatively, capillary end 34 may be blocked and carrier gas may be introduced via a separate inlet during MALDI operation.

Thus, a method of operation according to the present invention consists of the steps of:

a) forming a DC barrier in analysis section 145;
b) applying an RF field for focusing ions towards axis 153;
c) generating a group of MALDI ions via one or more pulses of laser light;
d) introducing a carrier gas into extended funnel 152;
e) accelerating ions into focusing section 143 by applying a potential to deflection electrode 239;
f) forcing said group of ions into analysis section 145 by applying a first set of DC potentials to the electrodes of focusing section 143;
g) inducing a carrier gas flow through channel 141 using a pump downstream from the exit end of funnel 152;
h) gradually reducing said DC barrier in analysis section 145 so as to allow said carrier gas flow to push ions from said group of ions over the DC barrier in order of the ions' mobilities;
i) focusing ions through the aperture in exit electrode 155; and
j) detecting ions that have been ejected from analysis section 145.

It should also be recognized that when a mobility analysis is not desired, ions can be transmitted through extended ion funnel 152 without manipulation. In such a case the RF potentials are applied to funnel 152 so as to focus the ions onto axis 153, also DC potentials are applied to electrodes 239 and 101-109 as shown in FIG. 8 so as to push ions into section 143. However, no axial DC field is applied in analysis section 145. The flow of gas is allowed to immediately carry ions through channel 141 and out exit end 167 of the funnel. Alternatively, the axial DC field is applied so as to push ions towards exit end 167. That is, in analysis section 145 the most repulsive DC potential is applied near the entrance end of section 145 and the most attractive DC potential are applied near the exit end of section 145.

In alternate embodiments, two or more extended funnel ion mobility analyzers may be used in series. In such an instrument, ions may be analyzed in a first extended funnel analyzer to determine the ions' mobility. The ions may then be reacted or activated in an intermediate device. For example, the ions may be collisionally activated so as to cause the ion to change conformation. The ions may then be analyzed in a second mobility analyzer to determine how the mobility of the selected ions has changed.

Alternatively, a first extended ion funnel may be operated within the low field limit and a second extended funnel operated in series with the first funnel may be operated above the low field limit. Ions are analyzed in the first extended funnel analyzer to determine the ions' mobility in the low field limit. The ions are then introduced into the second extended ion funnel analyzer to determine the ions' mobility above the low field limit.

In alternate embodiments, focusing section 143 may be eliminated and ions in a gas carrier gas may be injected directly into section 145. In further alternate embodiments, the axis of capillary 7 need not be oriented orthogonally to axis 153, rather the angle between the axis of capillary 7 and axis 153 may be any angle. In further alternate embodiments ions are not formed in the carrier gas, but are introduced into the carrier gas before the carrier gas, with ions entrained, is introduced into section 145. In yet further alternate embodiments, segmented electrodes 101-136 may be replaced with any other electrode structure capable of supporting a laminar flow an axial DC field, and a field that confines ions near axis 153.

The parallel flow ion mobility analyzer according to the present invention may be used without subsequent mass analysis. That is, ions may be detected following the mobility analysis without any further manipulation by other ion optical devices. In the same vein, in alternate embodiments, the parallel flow ion mobility analyzer according to the present invention may be built and used as a stand-alone device. That is, the mobility analyzer according to the present invention may be the only analyzer in alternate embodiment instruments. Alternatively, the mobility analyzer may be incorporated in instruments having any number of other mobility and/or mass analyzers.

While the present invention has been described with reference to one or more preferred and alternate embodiments, such embodiments are merely exemplary and are not intended to be limiting or to represent an exhaustive enumeration of all aspects of the invention. The scope of the invention, therefore, shall be defined solely by the following claims. Further, it will be apparent to those of skill in the art that numerous changes may be made in such details without departing from the spirit and the principles of the invention. It should be appreciated that the present invention is capable of being embodied in other forms without departing from its essential characteristics.

What is claimed is:

1. A combination spectrometer that analyzes ions by parallel flow ion mobility and by mass comprising:
   a mechanism that entrains the sample ions in a carrier gas;
   a mass spectrometer having a vacuum system with an extended ion funnel and a mass analyzer located inside the vacuum system;
   a mechanism that introduces the sample ions and the carrier gas into an entrance end of the extended ion funnel, the vacuum system drawing the carrier gas and the sample ions through the extended ion funnel to an exit end of the extended ion funnel and towards the mass analyzer;
   wherein the extended ion funnel is constructed with a plurality of segmented electrodes that are connected to an RF voltage source so that an ion focusing section is formed inside the extended ion funnel near the entrance end and an ion mobility analyzing section with an RF containment field is formed inside the extended ion funnel near the exit end and the sample ions are separated by ion mobility as they move through the extended ion funnel.

2. The apparatus of claim 1 wherein the mechanism that introduces the sample ions and the carrier gas into the extended ion funnel comprises an ion focusing section of the extended ion funnel that is connected to the RF voltage source so that a dipolar focusing RF field is generated therein.

3. The apparatus of claim 2 wherein the ion focusing section has an axis and is comprised of a plurality of segmented electrodes positioned perpendicular to, and spaced along, the axis.

4. The apparatus of claim 3 wherein spaces between adjacent electrodes comprising the ion focusing section are open so that the carrier gas may pass between the adjacent electrodes.

5. The apparatus of claim 4 wherein each of the plurality of electrodes comprising the ion focusing section has a central circular opening and wherein the plurality of electrodes have diameters that vary as a function of position along the axis.

6. The apparatus of claim 5 wherein the diameters of central openings of electrodes comprising the ion focusing section which are near the ion mobility analyzing section are smaller than the diameters of central openings of electrodes at which the ions and the carrier gas enter the ion focusing section.

7. The apparatus of claim 1 further comprising an ion source that generates the sample ions utilizing one of the group consisting of electrospray ionization, atmospheric pressure chemical ionization, atmospheric pressure photoionization, laser desorption ionization, matrix assisted laser desorption ionization, and desorption electrospray ionization.

8. The apparatus of claim 1 wherein the carrier gas is one of the group consisting of $N_2$, $O_2$, $CO_2$, $H_2O$, Ar, He, $CH_4$, and mixtures thereof.

9. The apparatus of claim 1 wherein the extended ion funnel has an ion focusing section that follows the ion mobility analyzing section in the direction of ion motion.

10. The apparatus of claim 1 wherein the ion mobility analyzing section has an axis and is comprised of a plurality of segmented electrodes positioned perpendicular to, and spaced along, the axis.

11. The apparatus of claim 10 wherein each of the plurality of electrodes comprising the analyzing section has a central circular opening and wherein the central openings of all of the electrodes have a same diameter.

12. The apparatus of claim 10 wherein each of the plurality of electrodes comprising the analyzing section has a central circular opening and wherein the plurality of electrodes have diameters that vary as a function of position along the axis.

13. The apparatus of claim 10 wherein gaskets are placed between adjacent electrodes comprising the analyzing section such that the electrodes and the gaskets form a gas tight channel along the axis.

14. The apparatus of claim 10 wherein each of the plurality of segmented electrodes comprising the analyzing section has four segments.

15. The apparatus of claim 10 wherein each of the plurality of segmented electrodes comprising the analyzing section has six segments.

16. The apparatus of claim 10 wherein each of the plurality of segmented electrodes comprising the analyzing section has one segment.

17. The apparatus of claim 1 wherein the mass analyzer comprises one of the group consisting of time-of-flight mass analyzers, quadrupole filters, Paul ion traps, quadrupole linear ion traps, ion cyclotron resonance mass analyzers, and orbitrap mass analyzers.

18. The apparatus of claim 1 wherein each of the plurality of segmented electrodes has four segments.

19. The apparatus of claim 1 wherein each of the plurality of segmented electrodes has one segment.

20. The apparatus of claim 1 further comprising a deflection electrode located in the vacuum system, positioned adjacent to the mechanism that introduces the sample ions and the carrier gas into the extended ion funnel and connected to a voltage source for directing the sample ions into the mechanism that introduces the sample ions and the carrier gas into the extended ion funnel.

21. The apparatus of claim 1 further comprising a sample located in the vacuum system, a laser located outside of the vacuum system, and a window in the vacuum system for allowing laser light generated by the laser to impinge on the sample.

22. A method for analyzing sample ions by parallel flow ion mobility spectrometry in combination with a mass spectrometer having,
    an ion source,
    a vacuum system having an extended ion funnel and a mass analyzer located therein,
    a deflection electrode located in the vacuum system that introduces the sample ions and the carrier gas into an entrance end of the extended ion funnel, the vacuum system drawing the carrier gas and the sample ions through the extended ion funnel to an exit end of the extended ion funnel and towards the mass analyzer,
    an extended ion funnel located in the vacuum system and having a plurality of segmented electrodes that are connected to voltage sources so that an ion focusing section is formed inside the extended ion funnel near the entrance end and an ion mobility analyzing section with an axis and an RF containment field is formed inside the extended ion funnel near the exit end and the sample ions are separated by ion mobility as they move through the extended ion funnel, and
    an ion detector,
the method comprising:
(a) forming a DC barrier in the ion mobility analyzing section;
(b) applying an RF voltage to the ion mobility analyzing section for focusing ions towards the axis;
(c) generating ions in the ion source;
(d) entraining generated ions in a carrier gas;
(e) pulsing a group of entrained ions into extended ion funnel focusing section by applying a pulsed electrical potential to the deflection electrode;
(f) forcing the group of ions into ion mobility analyzing section by applying a first set of DC potentials to electrodes of the ion focusing section;
(g) preventing additional ions from entering the ion mobility analyzing section by applying a second set of DC potentials to the deflection electrode and the electrodes of the ion focusing section;
(h) inducing a carrier gas flow through the ion mobility analyzing section away from the ion focusing section with a vacuum pump in the vacuum system;
(i) gradually reducing the DC barrier formed in step (a) to allow the carrier gas flow to push ions from the group of ions over the DC barrier in order of the ions' mobilities;
(j) focusing ions that have been pushed over the DC barrier with the second ion focusing section; and
(k) detecting ions that have been focused in step (j) with the ion detector.

* * * * *